(12) United States Patent
Enenkel et al.

(10) Patent No.: US 7,384,744 B2
(45) Date of Patent: Jun. 10, 2008

(54) EXPRESSION VECTOR, METHODS FOR THE PRODUCTION OF HETEROLOGOUS GENE PRODUCTS AND FOR THE SELECTION OF RECOMBINANT CELLS PRODUCING HIGH LEVELS OF SUCH PRODUCTS

(75) Inventors: Barbara Enenkel, Warthausen (DE); Juergen Fieder, Unterstadion (DE); Ralf Otto, Oggelshausen (DE); Stefanos Grammatikos, Uttenweiler (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 428 days.

(21) Appl. No.: 10/724,266

(22) Filed: Nov. 26, 2003

(65) Prior Publication Data

US 2004/0148647 A1 Jul. 29, 2004

Related U.S. Application Data

(60) Provisional application No. 60/431,536, filed on Dec. 6, 2002.

(30) Foreign Application Priority Data

Nov. 29, 2002 (DE) ................................ 102 56 083

(51) Int. Cl.
*C12Q 1/68* (2006.01)
(52) U.S. Cl. ............................ 435/6; 435/69.1; 435/358
(58) Field of Classification Search ....................... None
See application file for complete search history.

(56) References Cited

U.S. PATENT DOCUMENTS

| | | | |
|---|---|---|---|
| 4,656,134 | A | 4/1987 | Ringold |
| 5,122,458 | A | 6/1992 | Post et al. |
| 5,179,017 | A | 1/1993 | Axel et al. |
| 5,412,216 | A | 5/1995 | Dodson, Jr. |
| 5,491,084 | A | 2/1996 | Chalfie et al. |
| 6,060,273 | A | 5/2000 | Dirks et al. |
| 6,063,598 | A | 5/2000 | Enenkel et al. |
| 6,146,826 | A | 11/2000 | Chalfie et al. |
| 2003/0157641 | A1 | 8/2003 | Reff, et al. |
| 2003/0219871 | A1* | 11/2003 | Enenkel et al. ............. 435/69.1 |

FOREIGN PATENT DOCUMENTS

| | | |
|---|---|---|
| DE | 195 39 493 A1 | 4/1997 |
| DE | 19539493 A1 | 4/1997 |
| EP | 0393438 A2 | 10/1990 |
| EP | 0953639 A1 | 11/1999 |
| WO | 9208796 A1 | 5/1992 |
| WO | 9405785 A1 | 3/1994 |
| WO | 9428143 A1 | 12/1994 |
| WO | WO97/15664 | 5/1997 |
| WO | WO98/32869 | 7/1998 |
| WO | WO99/53046 | 10/1999 |
| WO | 0034318 A1 | 6/2000 |
| WO | 0034326 A1 | 6/2000 |
| WO | 0034526 A1 | 6/2000 |
| WO | WO 01/04306 A1 | 1/2001 |
| WO | 0127150 A2 | 4/2001 |
| WO | WO 02/094325 A2 | 11/2002 |

OTHER PUBLICATIONS

Charles G. Bailey et al; High-Throughput Clonal Selection of Recombinant CHO Cells Using a Dominant Selectable and Amplifiable Metallothionein-GFP Fusion Protein; Biotechnology and Biomolecular Dec. 20, 2002 vol. 7 p. 670-676; Wiley Periodicals, Inc.
Xuedong Liu et al; Generation of Mammalian Cells Stably Expressing Multiple Genes at Predetermined Levels; Analytical Biochemistry (2000) vol. 9 pp. 20-28; Academic Press.
Robert P. Bennett et al; Fusion of Green Fluorescent Protein with the Zeocin TM-Resistance Marker Allows Visual Screening and Drug Selection of Transfected Eukaryotic Cells; Biotecniques (Mar. 1998) vol. 24 No. 3 pp. 478-482; Invitrogen Corporation, Carlsbad, CA. USA.
Y. Gloria Meng et al; Green fluorescent protein as a second selectable marker for selection of high producing clones from transfected CHO cells; Gene (2000) vol. 242 pp. 201-207; Elsevier Science B.V.
D.D. Mosser et al; Use of a Dicistronic Expression Cassette Encoding the Green Fluorescent Protein for the Screening and Selection of Cells Expressing Inducible Gene Products; Biotechniques (Jan. 1997) vol. 22 No. 1 pp. 150-161; National Research Council, Montreal Canada.
No Soo Kim et al; Key Determinants in the Occurance of Clonal Variation in Humanized Antibody Expression of CHO Cells during Dihydrofolate Reductase Mediated Gene Amplification; Biotechnology Prog. (2001) vol. 17 pp. 69-75; American Chemical Society.
Rolf G. Werner et al; Appropriate Mammalian Expression Systems for Biopharmaceuticals; Drug Research (1998) vol. 8 pp. 870-880; Boehringer Ingelheim Pharma KG, Biberach Germany.
Gail Urlaub et al; Delection of the Diploid Dihydrofolate Reductase Locus from Cultured Mammalian Cells; Cell (Jun. 1983) vol. 33 pp. 405-412; Department of Biological Sciences Columbia University, New York, NY.
Yoshikazu Sugimoto et al; Efficient Expression of Drug-selectable Genes in Retroviral Vectors Under Control of an Internal Ribosome Entry Site; Biotechnology (Jul. 1994) vol. 12 pp. 694-698; National Cancer Institute.
N. Ramesh et al; High-titer bicistronic retroviral vectors employing foot-and-mouth disease virus internal ribosome entry site; Nucleic Acids Research (1996) vol. 24 no. 14 pp. 2697-2700; Oxford University Press.
Monique V. Davies et al; The Sequence Context of the Initiation Codon in the Encephalomyocarditis Virus Leader Modulates Efficiency of Internal Translation Initiation; Journal of Virology (Apr. 1992) vol. 66 No. 4 pp. 1924-1932; American Society for Microbiology.

(Continued)

*Primary Examiner*—James Ketter
(74) *Attorney, Agent, or Firm*—Michael P. Morris; Paula K. Wittmayer; Edouard G. Lebel

(57) ABSTRACT

An expression vector for eukaryotic cells comprising a gene which codes for a protein of interest, functionally linked to a hamster-ubiquitin/S27a-promoter and a gene which codes for a fluorescent protein. Preferably the expression vector also contains an amplifiable selectable marker gene. The invention also describes host cells, preferably mammalian cells, which have been transfected with the expression vector, processes for producing heterologous gene products and a method of selecting high-producing cells.

11 Claims, 9 Drawing Sheets

OTHER PUBLICATIONS

Mohammed A. Adam et al; Internal Initiation of Translation in Retroviral Vectors Carrying Picornavirus 5' Nontranslated Regions; Journal of Virology (Sep. 1991) vol. 65 No. 9 pp. 4985-4990; American Society for Microbiology.

Randal J. Kaufman et al; Amplification and Expression of Sequences Cotransfected with a Modular Dihydrofolate Reductase Complementary DNA Gene; J. Mol. Biol. (1982) vol. 159 pp. 601-621; Center for Cancer Research and Department of Biology, Cambridge Mass.

International Search Report Refernce No. PCT/EP 03/13225, (2003).

Michael Primig 1 et al; A novel GFPneo vector designed for the isolation and analysis of enhancer elements in transfected mammalian cells; International Journal of Genes and Genomes (1998) vol. 215 pp. 181-189; Elsevier Science B.V.

Jerry Pelletier et al; Internal initiation of translation of eukaryotic mRNA directed by a sequence derived from poliovirus RNA; Nature (Jul. 1988) vol. 334 pp. 320-325; Department of Biochemistry McGill Cancer Center, McGill University Montreal Canada.

Richard A. Morgan et al: Retroviral vectors containing putative internal ribosome entry sites; development of a polycistronic gene transfer system and applications to human gene therapy; Nucleic Acids Research (Feb. 10, 1992) vol. 20 No. 6 pp. 1293-1299; Molecular Hematology Branch, Bethesda MD.

Lucia Monaco et al; Expression of recombinant human granulocyte colony-stimulating factor in CHO dhfr -cells: new insights into the in vitro amplification expression system; Gene (1996) vol. 180 pp. 145-150; Elsevier Science B.V.

Victor V. Levenson et al; Internal Ribosomal Entry Site-Containing Retroviral Vectors with Green Fluorescent Protein and Drug Resistance Markers; Human Gene Therapy (May 20, 1998) vol. 9 pp. 1233-1236: Department of Molecular Genetics, University of IL, Chicago, IL.

Randal J. Kaufman; Selection and Coamplification of Heterologous Genes in Mammalian Cells; Methods in Enzymology vol. 185 No. 42 pp. 537-566; Academic Press, Inc. 1982.

Sung K. Jang et al; Initiation of Protein Synthesis by Internal Entry of Ribosomes in to the 5' Nontranslated Region of Encephalomyocarditis Virus RNA In Vitro; Journal of Virology (Apr. 1989) vol. 63 No. 4 pp. 1651-1660; American Society for Microbiology.

Cord Hemann et al; High-Copy Expression Vector Based on Amplification-Promoting Sequences; DNA and Cell Biology (1994) vol. 13 No. 4 pp. 437-445; Mary Ann Liebert, Inc Publishers.

Alexander N. Gubin et al; Long-Term, Stable Expression of Green Fluorescent Protein in Mammalian Cells; Biochemical and Biophysical Research Communications (1997) vol. 236 pp. 347-350; Academic Press.

Martin Chalfie et al; Green Fluorescent Protein as a Marker for Gene Expression; Science (Feb. 11, 1994) vol. 263 pp. 802-805; Department of Biological Sciences, Columbia University New York, NY.

Manfred Gossen et al; Inducible Gene Expression Systems for Higher Eukaryotic Cells; Current Opinion in Biotechnology (1994) vol. 5 pp. 516-520; Current Biology Ltd.

Shi-Zhen Hu et al; Minibody: A Novel Engineered Anti-Carcinoembryonic Antigen Antibody Fragment (Single-Chain Fv-CH3) which Exhibits Rapid, High-Level Targeting of Xenografts; Cancer Research (1996) vol. 56 pp. 3055-3061.

James S. Huston et al; Protein Engineering of Antibody Binding Sites: Recovery of Specific Activity in an Anti-Digoxin Single-Chain Fv Analogue Produced in *Excherichia Coli*; Proceedings of the National Academy of Sciences of the United States of America (1988) vol. 85 pp. 5879-5883.

Alexander A. Kortt et al; Single-Chain Fv Fragments of Anti-Neuraminidase Antibody NC10 Containing Five- and Ten-Residue Linkers Form Dimers and with Zero-Residue Linker a Trimer; Protein Engineering (1997) vol. 10 No. 4 pp. 423-433.

Brett Lovejoy et al; crystal structure of a Synthetic Triple-Stranded Helical Bundle; Research Article (1993) vol. 259 pp. 1288-1293.

Yasumi Ohshima et al; Signals for the Selection of a Splice in Pre-mRNA Computer Analysis of Splice Junction Sequences and Like Sequences; Journal Molecular Biology (1987) vol. 195 pp. 247-259.

Peter Pack et al; Tetravalent Miniantibodies with High Avidity Assembling in *Escherichia Coli*; Journal Molecular Biology (1995) vol. 246 pp. 28-34; Academic Press Limited.

Olga Perisic et al; Crystal Structure of a Diabody, a Bivalent Antibody Fragment; Structure (1994) vol. 2 pp. 1217-1226; Current Biology Ltd.

M. Wigler et al; Transformation of Mammalian Cells with an Amplifiable Dominant-Acting Gene; Proceedings of the National Academy of Sciences of the United States of America (1980) vol. 77 No. 6 pp. 3567-3570.

Jordi Bella et al; Review: Rhinoviruses and Their ICAM Receptors; Journal of Structural Biology (1999) vol. 128 pp. 69-74; Academic Press.

Steven D. Marlin et al; A Soluble Form of Intercellular Adhesion Molecule-1 Inhibits Rhinovirus Infection; Nature (1990) vol. 344 pp. 70-77.

Garry P. Nolan et al; Fluorescence-Activated Cell Analysis and Sorting of Viable Mammalian Cells based on B-D-Galactosidase Activity After Transduction of *Escherichia Coli* LacZ ; Proceedings of the National Academy of Sciences of the United States of America (1988) vol. 85 pp. 2603-2607.

Christian C. Simonsen et al; Isolation and Expression of an Altered Dihydrofolate Reductase cDNA; Proceedings of the National Academy of Sciences of the United States of America (1983) vol. 80 pp. 2495-2499.

Steffen Faisst et al; Compilation of Vertebrate-Encoded Transcription Factors; Nucleic Acids Research (1992) vol. 20 No. 1 pp. 3-26; Oxford University Press.

Peter Pack et al; Improved Bivalent Miniantibodies, with identical Avidity as whole Antibodies, Produced by High Cell Density Fermentation of *Escherichia Coli*; Bio/Technology (1993) vol. 11 pp. 1271-1277; Nature Publishing Group.

Daniel A Haber et al; Chromosome-Mediated Transfer and Amplification of an Altered Mouse Dihydrofolate Reductase Gene; Somatic Cell Genetics (1982) vol. 8 No. 4 pp. 499-508; Plenum Publishing Corporation.

Austrian Search Report and Written Opinion for 200503275-0, mailed Sep. 7, 2006.

* cited by examiner

SEQUENCE LISTING

```
<160> NUMBER OF SEQ ID NOS: 1

<210> SEQ ID NO 1
<211> LENGTH: 2406
<212> TYPE: DNA
<213> ORGANISM: Cricetulus griseus
<300> PUBLICATION INFORMATION:
<310> PATENT DOCUMENT NUMBER: PCT/EP/96/04631
<311> PATENT FILING DATE: 1996-10-24
<312> PUBLICATION DATE: 1997-05-01

<400> SEQUENCE: 1
gatctccagg  acagccatgg  ctattacaca  gagaaaccct  gtctggaaaa  acaaaaaatt      60
agtgtccatg  tgtaaatgtg  tggagtatgc  ttgtcatgcc  acatacagag  gtagagggca     120
gtttatggga  gtcagttcct  attcttcctt  tatgggggac  ctggggactg  aactcaggtc     180
atcaggcttg  gcagaaagtg  cattagctca  cggagcctta  tcattggcga  aagctctctc     240
aagtagaaaa  tcaatgtgtt  tgctcatagt  gcaatcatta  tgtttcgaga  ggggaagggt     300
```

```
acaatcgttg gggcatgtgt ggtcacatct gaatagcagt agctccctag gagaattcca      360
agttctttgg tggtgtatca atgcccttaa aggggtcaac aacttttttt ccctctgaca      420
aaactatctt cttatgtcct tgtccctcat atttgaagta ttttattctt tgcagtgttg      480
aatatcaatt ctagcacctc agacatgtta ggtaagtacc ctacaactca ggttaactaa      540
tttaatttaa ctaatttaac cccaacactt tttctttgtt tatccacatt tgtggagtgt      600
gtgtgtgtgt gtgtgtgtgt gtgtgtgtgt gtgtgtgtgt gtgtgtgtgc                660
gcgcgcgcgc gcgctcggat cattctacct tttgtttaaa aaatgttagt ccaggggtgg      720
ggtgcactgt gaaagtctga gggtaacttg ctggggtcag ttctttccac tataggacag      780
aactccaggt gtcaactctt tactgacaga accatccaaa tagccctatc taattttagt      840
tttttattta tttattttt gttttcgag acagggtttc tctgtggctt tggaggctgt      900
cctggaacta gctcttgtag accaggctgg tctcgaactc agagatccac ctgcctctgc      960
ctcctgagtc tgggattaa aggcatgcgc caccaacgct tggctctacc taattttaaa     1020
agagattgtg tgtcacaagg gtgtcatgtc gccctgcaac cacccccccc ccaaaaaaaa     1080
aaaaaaaaaa acttcactga agctgaagca cgatgatttg gttactctgg ctggccaatg     1140
agctctaggg agtctcctgt caaacagaat ctcaacaggc gcagcagtct tttttaaagt     1200
ggggttacaa cacaggtttt tgcatatcag gcattttatc taagctattt cccagccaaa     1260
aatgtgtatt ttgggaggcag cagagctaat agattaaaat gagggaagag cccacacagg     1320
ttattaggaa gataagcatc ttctttatat aaaacaaaac caaaccaaac tggaggaggt     1380
ctacctttag ggatggaaga aaagacattt agagggtgca atagaaaggg cactgagttt     1440
gtgaggtgga ggactgggag agggcgcaac cgctttaact gtcctgtttt gcctattttt     1500
tggggacagc acatgttcct attttttccca ggatgggcaa tctccacgtc caaacttgcg     1560
gtcgaggact acagtcattt tgcaggtttc cttactgtat ggcttttaaa acgtgcaaag     1620
gtgaccatta accgtttcac gctgggaggg cacgtgcggc tcagatgctt cctctgactg     1680
agggccagga gggggctaca cggaagaggc cacacccgca cttgggaaga ctcgatttgg     1740
gcttcagctg gctgagacgc cccagcaggc tcctcggcta caccttcagc cccgaatgcc     1800
ttccggccca taacccttcc cttctaggca ttttccggcga ggacccaccc tcgcgccaaa     1860
cattcggccc catcccccgg tcctcacctg aatctctaac tctgactcca gagtttagag     1920
actataacca gatagcccgg atgtgtggaa ctgcatcttg ggacgagtag ttttagcaaa     1980
aagaaagcga cgaaaaacta caattcccag acagacttgt gttacctctc ttctcatgct     2040
aaacaagccc cctttaaagg aaagcccctc ttagtcgcat cgactgtgta agaaaggcgt     2100
ttgaaacatt ttaatgttgg gcacaccgtt tcgaggaccg aaatgagaaa gagcataggg     2160
aaacggagcg cccgagctag tctggcactg cgttagacag ccgcggtcgt tgcagcgggc     2220
aggcacttgc gtgacgcct aaggggcggg tcttccggcc gggaagcccc gttggtccgc     2280
gcggctcttc ctttccgatc cgccatccgt ggtgagtgtg tgctgcgggc tgccgctccg     2340
gcttggggct tcccgcgtcg ctctcaccct ggtcggcggc tctaatccgt ctcttttcga     2400
atgtag                                                                2406
```

EXPRESSION VECTOR, METHODS FOR THE PRODUCTION OF HETEROLOGOUS GENE PRODUCTS AND FOR THE SELECTION OF RECOMBINANT CELLS PRODUCING HIGH LEVELS OF SUCH PRODUCTS

RELATED APPLICATIONS

The priority benefit of DE 102 56 083.8, filed Nov. 29, 2002 and U.S. Provisional Application No. 60/431,536, filed Dec. 6, 2002 are hereby claimed, both which are incorporated by reference herein.

SCOPE OF THE INVENTION

The invention relates to a method for selecting highly productive recombinant cells, a method for preparing heterologous gene products and expression vectors and host cells transfected therewith which may be used in these processes.

BACKGROUND TO THE INVENTION

Mammalian cells are the preferred host cells for the production of complex biopharmaceutical proteins as the modifications carried out post-translationally are compatible with humans both functionally and pharmacokinetically. Commercially relevant cell types are hybridoma, myeloma CHO (Chinese Hamster Ovary) cells and BHK (Baby Hamster Kidney) cells. The cultivation of the host cells is increasingly carried out under serum- and protein-free production conditions. The reasons for these are the concomitant cost reduction, the reduced interference in the purification of the recombinant protein and the reduction in the potential for the introduction of pathogens (e.g. prions and viruses). The use of CHO cells as host cells is becoming more widespread as these cells adapt to suspension growth in serum- and protein-free medium and are also regarded and accepted as safe production cells by the regulatory authorities.

In order to produce a stable mammalian cell line which expresses a heterologous gene of interest, the heterologous gene is generally inserted in the desired cell line together with a selectable marker gene such as e.g. neomycin phosphotransferase by transfection. The heterologous gene and the selectable marker gene can be expressed either together by a single vector or by separate vectors which are cotransfected. Two to three days after transfection the cells are transferred into medium containing a selective agent, e.g. G418 when using neomycin phosphotransferase-gene, and cultivated for some weeks under these selective conditions. The emergent resistance cells can then be isolated and investigated for expression of the desired gene product. As a result of the random and undirected integration into the host cell genome a population of cells is obtained which have completely different rates of expression of the heterologous gene. These may also include non-expressing cells in which the selectable marker is expressed but not the gene of interest. In order to identify cell clones which have a very high expression of the heterologous gene of interest, it is therefore necessary to examine and test a large number of clones, which is time consuming, labour intensive and expensive.

Gene amplification is a widespread phenomenon in animal cell cultures, which is used for the production of recombinant biopharmaceutical proteins. The gene amplification drastically improves the originally relatively low productivity of numerous mammalian cell lines. One amplification technique which is widely used is dihydrofolate reductase (DHFR)-based gene amplification system which is very often used in DHFR-deficient Chinese Hamster Ovary (CHO) cells. The DHFR-deficient CHO cells, e.g. CHO-DUKX (ATCC CRL-9096) or CHO-DG44 (Urlaub, G. et al., *Cell* 1983, 33, 405-412), are transfected with a suitable vector system which codes for DHFR and the protein of interest. Then the transfectants are selected in a medium without glycine, hypoxanthine and thymidine. The amplification and hence the establishment of highly productive cell lines is achieved by the increasing addition of methotrexate (MTX), an inhibitor of dihydrofolate reductase (Kaufman, R. J. et al., *J Mol Biol* 1982, 159, 601-621; U.S. Pat. No. 4,656,134). The subsequent selection of the highly productive cells obtained is also subject to the principle of chance and is based on probabilities, as a result of which this selection step is highly labour-intensive and time-consuming.

All kinds of methods have been developed for monitoring gene transformation and expression better and more rapidly. These include, first of all, the use of reporter molecules such as chloramphenicol-acetyltransferase, luciferase, β-galactosidase or fusion proteins which contain the coding regions of β-galactosidase or luciferase. The disadvantage of these reporter gene assays is that the cells have to be fixed or lysed and have to be incubated with exogenously added substrates and co-factors. Thus, further cultivation of the analysed cells is out of the question. A more recent method based on the co-expression of the *E.coli* enzyme β-galactosidase does indeed allow lysed cells to be sorted using a FACS apparatus (Nolan, G. P. et al., *Proc Natl Acad Sci USA* 1988, 85, 2603-2607), but hypotonic pretreatment is required in order to charge the cells with the fluorogenic substrate. This activity also has to be inhibited before the FACS-based sorting.

With the introduction of green fluorescent protein (GFP) from *Aequorea victoria* and the GFP mutants developed therefrom as reporter molecule it became much easier to identify cells which express a heterologous gene. Co-expression of GFP allowed real-time analysis in vivo and sorting of transfectants on the basis of their fluorescence without the need for additional substrates or co-factors. The use of GFP as a reporter molecule for monitoring gene transfer has been described in various publications. In U.S. Pat. Nos. 5,491,084 and 6,146,826, Chalfie et al. described a method of selecting cells which express a protein of interest. This method comprises co-transfection of cells by a DNA molecule which contains the coding sequence for the protein of interest, and a second DNA-molecule which codes the GFP-gene. Then the GFP-expressing cells are selected. Gubin et al. investigated the stability of GFP expression in CHO cells in the absence of selective growth conditions (Gubin, A. N. et al., *Biochem Biophys Res Commun* 1997, 236, 347-350). The cells were transfected with a plasmid which contained both GFP and neomycin phosphotransferase. Mosser et al. used a plasmid which contained a bicistronic expression cassette coding for a GFP and a target gene (also known as the gene of interest) to identify and select cells which expressed inducible product (Mosser, D. D. et al., *BioTechniques* 1997, 22, 150-161). The target gene was under the control of a regulatable promoter. The coupling of the GFP and target gene expression was achieved using a viral IRES (Internal Ribosome Entry Site) element, as a result of which a bicistronic mRNA which coded for GFP and the protein of interest was expressed. The plasmid used did not itself contain any selectable marker gene. This was therefore introduced by a second plasmid in a co-transfection or in a subsequent transfection. By contrast, Levenson et al. used retroviral vectors with a bicistronic expression cassette in which the gene of interest can be cloned in front of the IRES sequence (Levenson, V. V. et al., *Human Gene Therapy* 1998, 9, 1233-1236). The sequence following the IRES sequence, on the other hand, coded for a selectable marker gene, this being a marker which conferred resistance to G418, puromycin, hygromycin B, histidinol D or phleomycin, or it was GFP.

Vectors have already also been described which contain an IRES element from the family of the picorna viruses, the IRES element being positioned between the product gene and a selectable marker gene (Pelletier, J. et al., *Nature* 1988, 334, 320-325; Jang, S. K. et al., *J Virol* 1989, 63, 1651-1660; Davies, M. V. et al., *J Virol* 1992, 66, 1924-1932).

GFP has also been successfully fused with resistance marker genes. For example, Bennett et al. describe a GFP/zeomycin fusion protein (Bennett, R. P. et al., *BioTechniques* 1998, 24, 478-482). This bifunctional selectable marker was successfully used to identify and select transfected mammalian cells. Primig et al. on the other hand used a fusion protein of GFP and neomycin phosphotransferase for their enhancer studies (Primig, M. et al., *Gene* 1998, 215, 181-189).

In the publication by Meng et al. and in International Patent application WO 01/04306, an expression system in which the gene of interest was expressed together with the amplifiable selectable marker gene DHFR and a GFP gene from a single vector was used to select and identify cells with a high expression of a recombinant protein (Meng, Y. G. et al., *Gene* 2000, 242, 201-207). The three genes were either combined in one transcription unit or divided between two units. This spatial and transcriptional linking of all three genes in a single expression vector was intended to increase their probability of co-amplification under selection pressure and thus identify and select high producing clones. The best clones which were isolated by using the combined selection by means of amplifiable DHFR selection markers and GFP-based FACS sorting expressed the protein of interest in an order of magnitude of not more than 3 to 4.5 pg per cell per day. The experiments were carried out with adherent cells and in serum-containing medium, i.e. with cells and under conditions which are known to be substantially more robust and are characterised by higher basic productivities.

SUMMARY OF THE INVENTION

The aim of the present invention was therefore to develop a selection system for recombinant cells with increased productivity, which meets the following requirements:

(1) A reduction in the time taken to develop high producing cells to produce biopharmaceutical proteins while at the same time lowering the development costs;
(2) A high throughput in the selection of high producing cells with low expenditure on capacity;
(3) The use of "fermentation-robust" high-producing cells which exhibit, for example, lower impairment of growth at increased methotrexate concentrations;
(4) The transfection, selection and cultivation of the suspension-adapted cells, preferably in serum-free medium;
(5) A reduction in the gene amplification steps required.

A further aim of the invention was to provide expression vectors and host cells transfected therewith which can be used in this clone selection system, as well as a process for preparing heterologous gene products using these host cells.

These objectives are achieved according to one aspect of the present invention by means of an expression vector which comprises a gene coding for a protein of interest (hereinafter also referred to as the "gene of interest") functionally linked to a hamster ubiquitin/S27a promoter and a gene which codes for a fluorescent protein.

The expression vector preferably also contains an amplifiable selection marker gene, e.g. the gene for dihydrofolate reductase (DHFR). A preferred expression vector also contains other regulatory elements, e.g. an enhancer functionally linked to the promoter. In addition, the expression vector preferably also contains an internal ribosomal entry site (IRES) which allows bicistronic expression of the gene which codes for a fluorescent protein and of the gene of interest.

The invention also relates to basic vectors which instead of the gene of interest have a multiple cloning site for the incorporation of such a gene, i.e. a sequence area with multiple cutting sites for restriction endonucleases.

In another aspect the present invention relates to host cells which have been transfected with one of the expression vectors mentioned. These are eukaryotic host cells, preferably mammalian cells, while rodent cells such as hamster cells and especially CHO cells or BHK cells are particularly preferred.

In another aspect the present invention relates to a process for preparing a heterologous gene product in which a host cell transfected with the expression vector according to the invention is cultivated under conditions which allow expression of the gene product and the gene product is isolated from the culture or the culture medium.

In one particular embodiment of the invention the host cell is transfected, preferably co-transfected, with the expression vector according to the invention and additionally with one or more vectors with genes which code for one or more other proteins of interest.

In this connection the present invention provides a process for preparing a heterodimeric protein in which a host cell of this kind which has been co-transfected with expression vectors which code for different subunits of the heterodimeric protein is cultivated under conditions which allow expression of the heterodimeric protein, and the heterodimeric protein is isolated from the culture or culture medium. One particular application for such a process is the production of antibodies and their subunits.

In another aspect the present invention relates to a process for selecting a host cell which expresses a protein of interest in which a population of host cells which have been transfected with an expression vector according to the invention is cultivated under conditions which allow expression of the protein of interest and of the fluorescent protein, and the cell or cells which exhibit the highest expression rates of fluorescent protein are identified and/or selected. The selection is preferably made using a fluorescence-activated cell sorter (FACS).

Surprisingly, it has been found that using the system provided according to the invention it is possible in a very short time to isolate cell pools which express average specific productivities of more than 15 pg (single-chained protein) or 10 pg (humanised antibody) of recombinant protein per cell and per day, without a gene amplification step. The specific productivities could be increased to more than 30 pg per cell and per day by a single DHFR-based gene amplification step. The productivities achieved in the cell pools are hence higher than the maximum productivities of the best cell clones published hitherto by a factor of 8 to 10.

Astonishingly, there is also a very good correlation between the expression of the protein of interest and the fluorescent protein. This is even true in the case of co-transfection if—as with an expressed antibody—the two immunoglobulin chains are each expressed by their own vector and in the FACS sorting a selection can only be made for the expression of the one chain, on account of its transcriptional coupling to the fluorescent protein. The high expression rates of the fluorescent protein have no negative effect whatsoever on the growth and vitality of the cells. In addition, the development time for selecting high producing cells can be reduced by at least half compared with a conventional stepwise gene amplification strategy, resulting in a significant reduction in the development capacity and costs.

"sICAM" codes for the soluble intracellular adhesion molecule (U.S. Pat. No. 5,412,216), whereas "F19HC" and "F19LC" code for the heavy and light chains, respectively of the humanised antibody F19 (EP 953 639).

Figure 4:
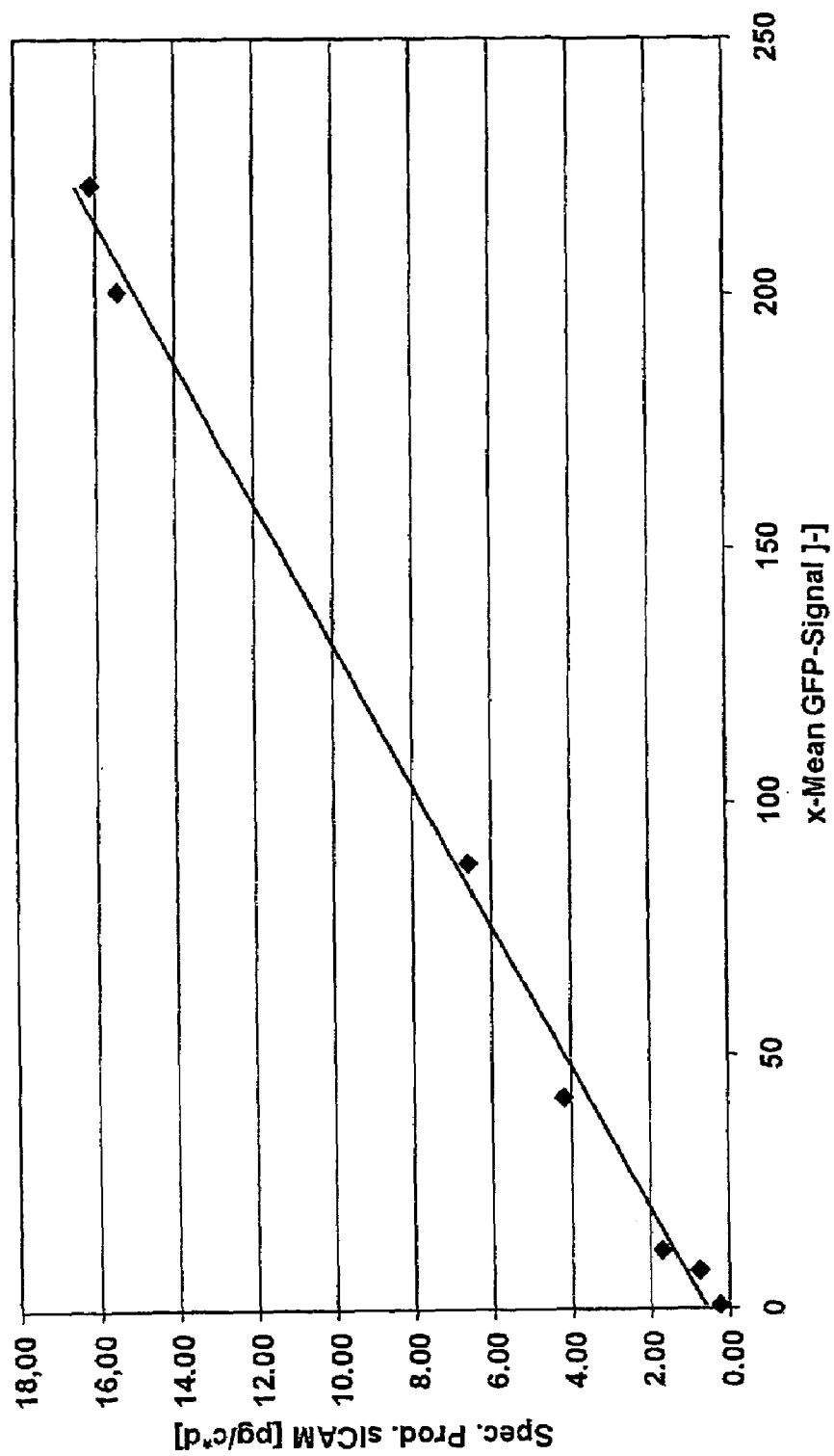

FIG. 4 shows the correlation between the sICAM productivity and the GFP fluorescence taking the cell pool ZB1 as an example. This cell pool was obtained from the transfection with the vector pBIDG-sICAM, in which the therapeutic protein sICAM and GFP are jointly expressed by a bicistronic transcription unit. The pool was subjected to a sequential GFP-based FACS sorting. After each sorting step (sort) the concentration of the sICAMs in the cell culture supernatant of the pool was determined by ELISA and the specific productivity per cell and per day was calculated (pg/c/d). Each data point is the average of at least three cultivation runs. A total of six sorts were carried out.

Figure 5:
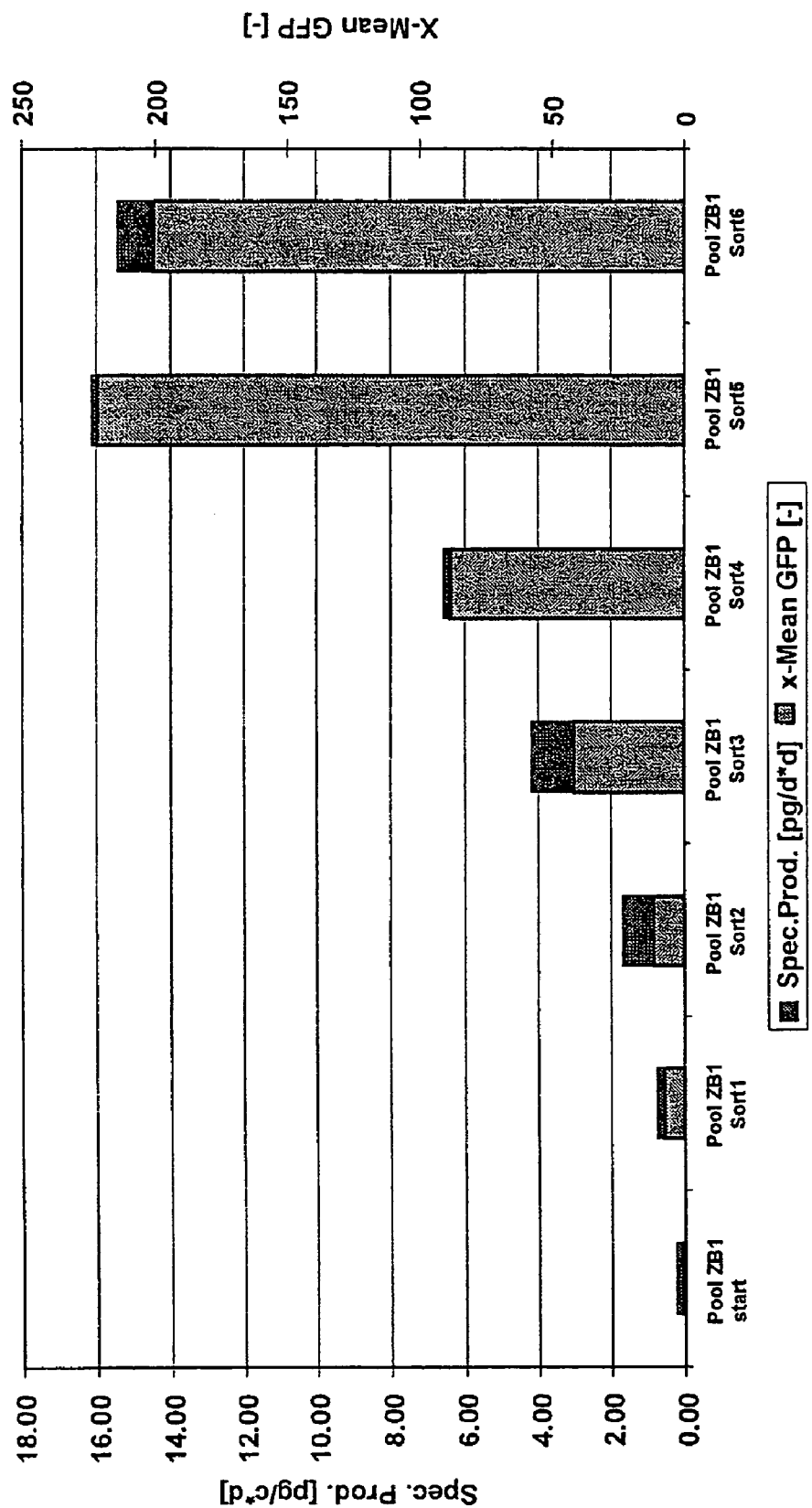

FIG. 5 shows the isolation of high-expressing sICAM cells by GFP-based FACS sorting taking the cell pool ZB1 as an example. This cell pool was obtained from the transfection with the vector pBIDG-sICAM in which the therapeutic protein sICAM and GFP are together expressed by a bicistronic transcription unit. The pool was subjected to sequential GFP-based FACS sorting. After each sort the concentration of the sICAM in the cell culture supernatant of the pool was determined by ELISA and the specific productivity per cell and per day (pg/c/d) was calculated. Each datapoint represents the average of at least three cultivation runs. In all, six sorts were carried out.

Figure 6:
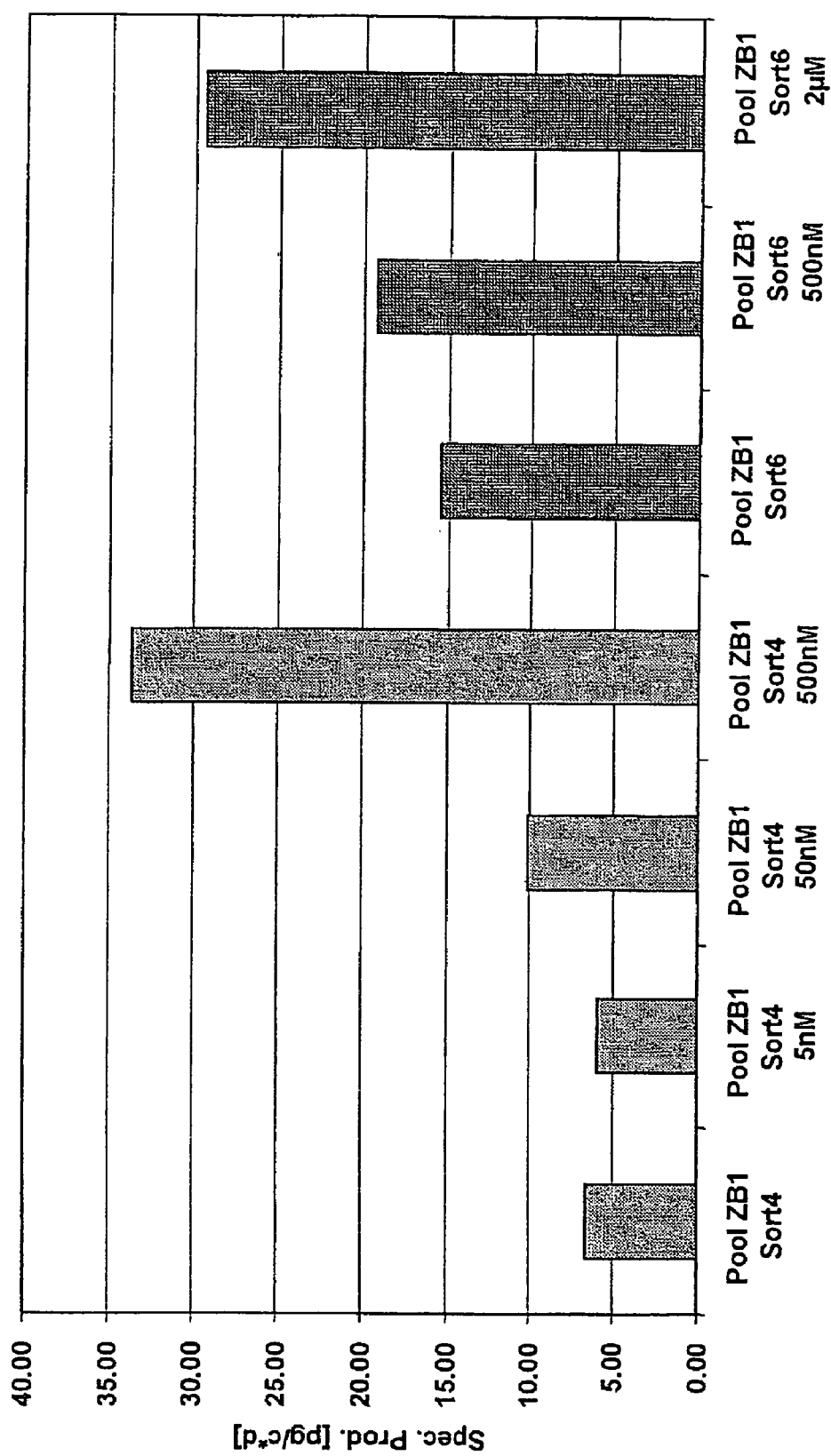

FIG. 6 shows the increase in sICAM productivity achieved by combining GFP-based selection with an MTX amplification step, taking the cell pool ZB1 as an example. This cell pool, which was obtained from the transfection with the vector pBIDG-sICAM, was subjected to sequential GFP-based FACS sorting. After the fourth sort and sixth sort a DHFR-mediated gene amplification was carried out by adding methotrexate (MTX) to the cultivation medium (5 nM, 50 nM, 500 nM or 2 µM MTX). The concentration of the sICAMs in the cell culture supernatant of the pool was determined by ELISA and the specific productivity per cell and per day (pg/c/d) was calculated. Each datapoint represents the average of at least three cultivation runs.

Figure 7:
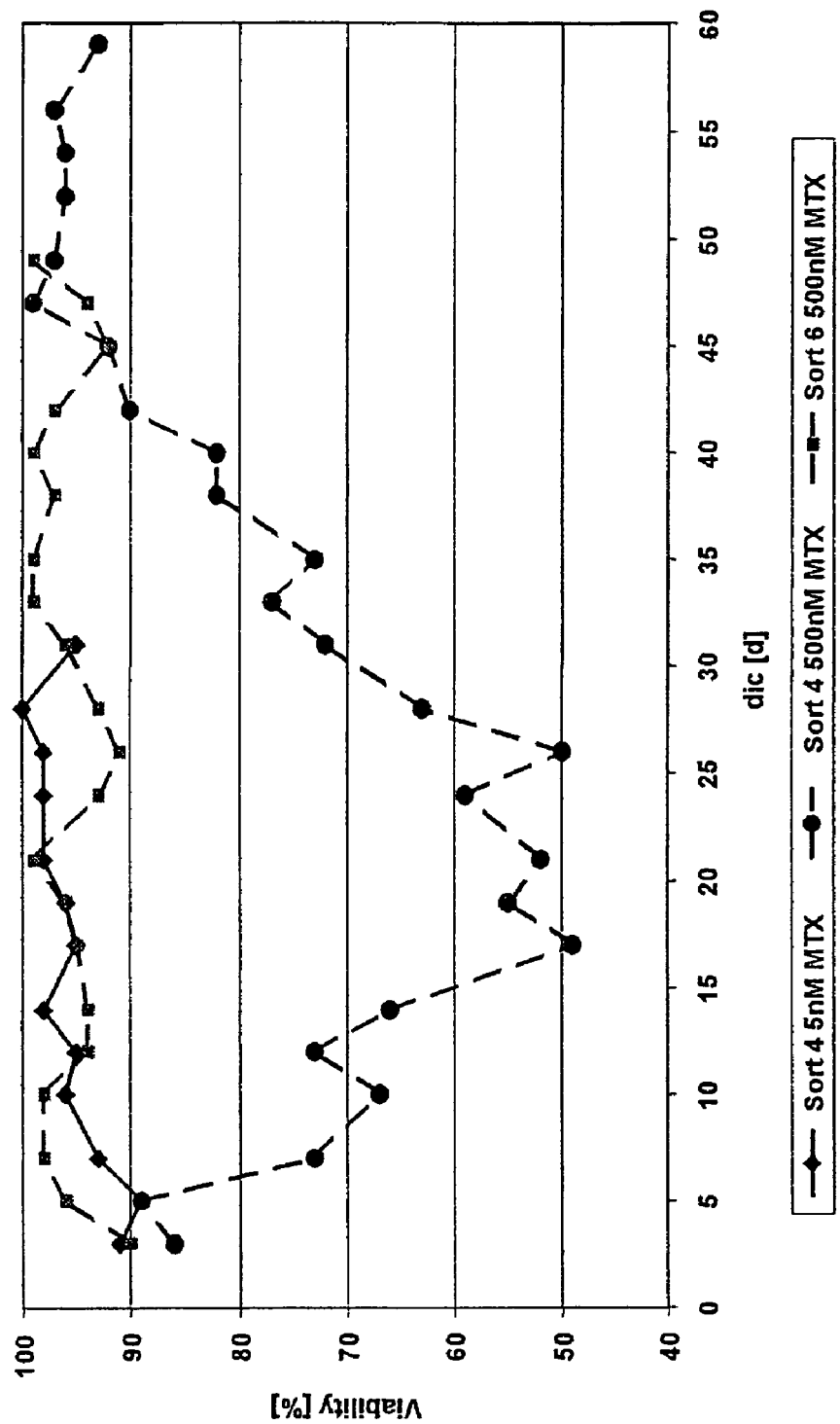

FIG. 7 shows the viability pattern of cell pools after the addition of different doses of methotrexate to the cultivation medium. The cell pool ZB1 which was obtained by transfection with the vector pBIDG-sICAM (FIG. 3) was subjected to sequential GFP-based FACS sorting. After the fourth sort and sixth sort a DHFR-mediated gene amplification was carried out by adding methotrexate (MTX) to the cultivation medium. The cell numbers and viability were determined during the selection phase by staining with tryptan blue and monitored over a number of days in cultivation (dic).

Figure 3:
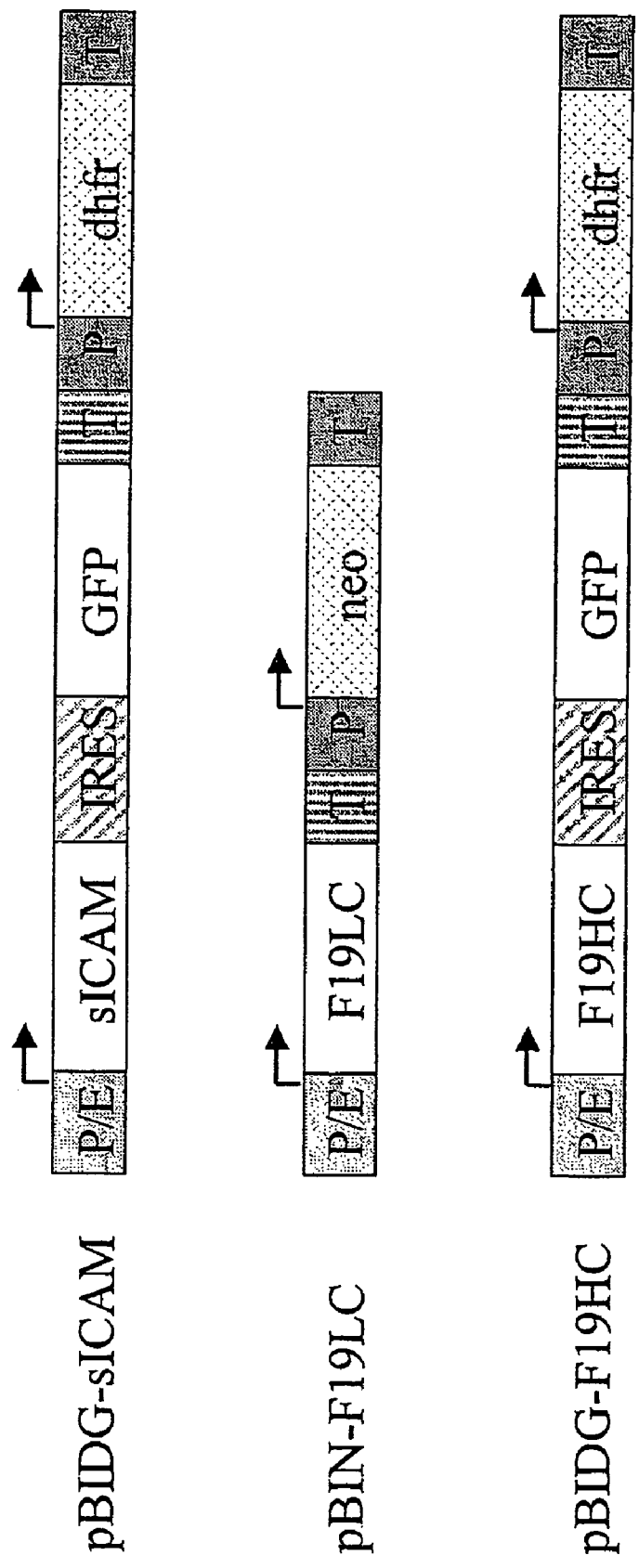
FIG. 3 is a diagrammatic representation of the eukaryotic expression vectors each of which codes for a biopharmaceutical protein and has been used to transfect CHO-DG44 cells. "P/E" is a combination of CMV enhancer and hamster-ubiquitin/S27a promoter, "P" on its own indicates a promoter element and "T" is a termination signal for transcription, which is needed for the polyadenylation of the transcribed mRNA. The position and direction of transcription initiation within each transcription unit is indicated by an arrow. The amplifiable selectable marker dihydrofolate reductase is abbreviated to "dhfr" and the selectable marker neomycin phosphotransferase is abbreviated to "neo". The "IRES" element coming from the encephalomyocarditis virus acts as an internal ribosomal entry site within the bicistronic transcription unit and enables translation of the following green fluorescent protein "GFP".
Figure 8:
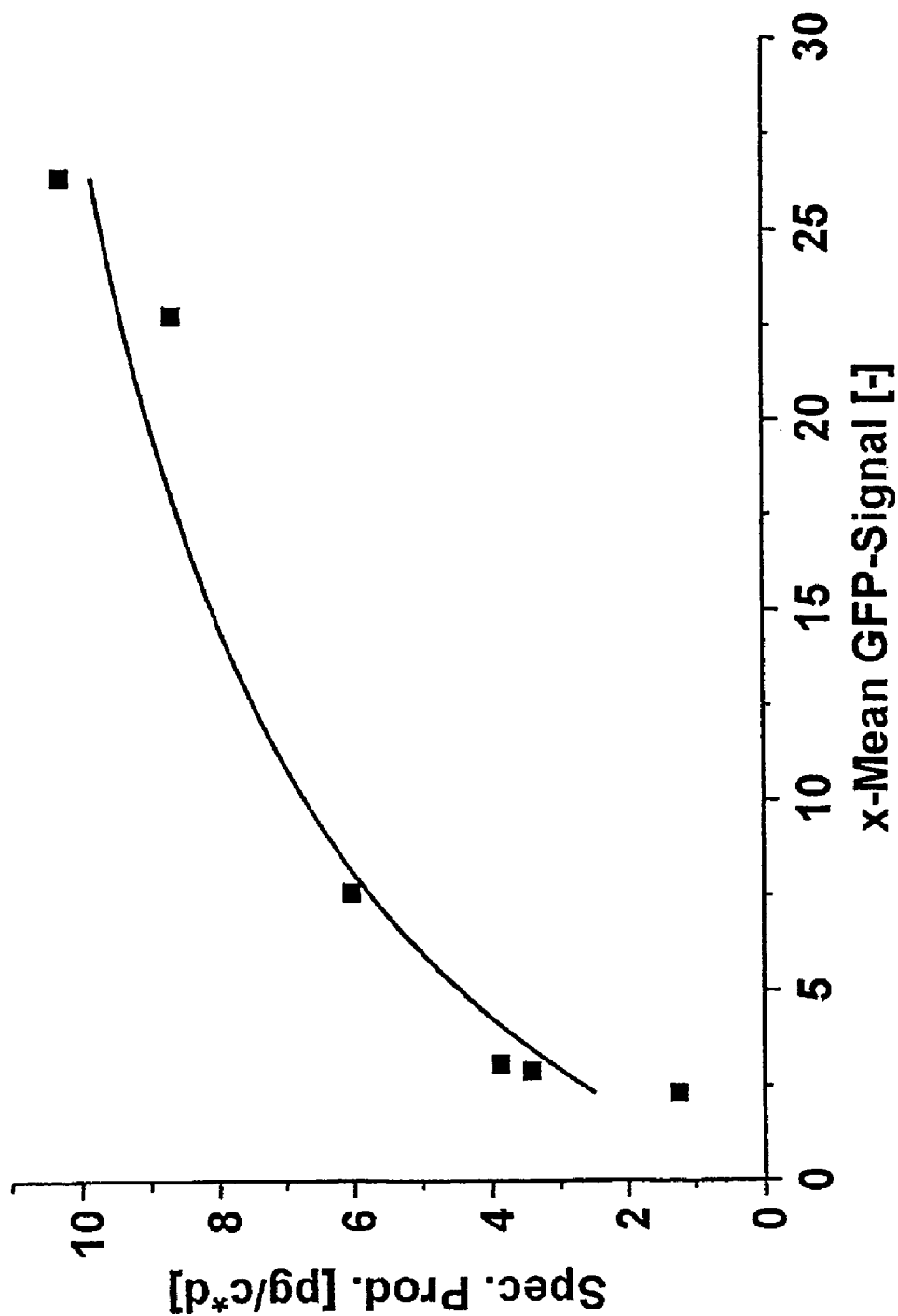

FIG. 8 shows the correlation between the antibody productivity (mAb F19) and the GFP fluorescence taking the cell pool ZB1 as an example. This cell pool was obtained from the transfection with the vector combination pBIDG-F19HC and pBIN-F19LC (FIG. 3). The pool was subjected to sequential GFP-based FACS sorting. After each sort the concentration of the antibody F19 in the cell culture supernatant of the pool was determined by ELISA and the specific productivity per cell and per day (pg/c/d) was calculated. Each datapoint represents the average of at least three cultivation runs. In all, six sorts were carried out.

Figure 9:
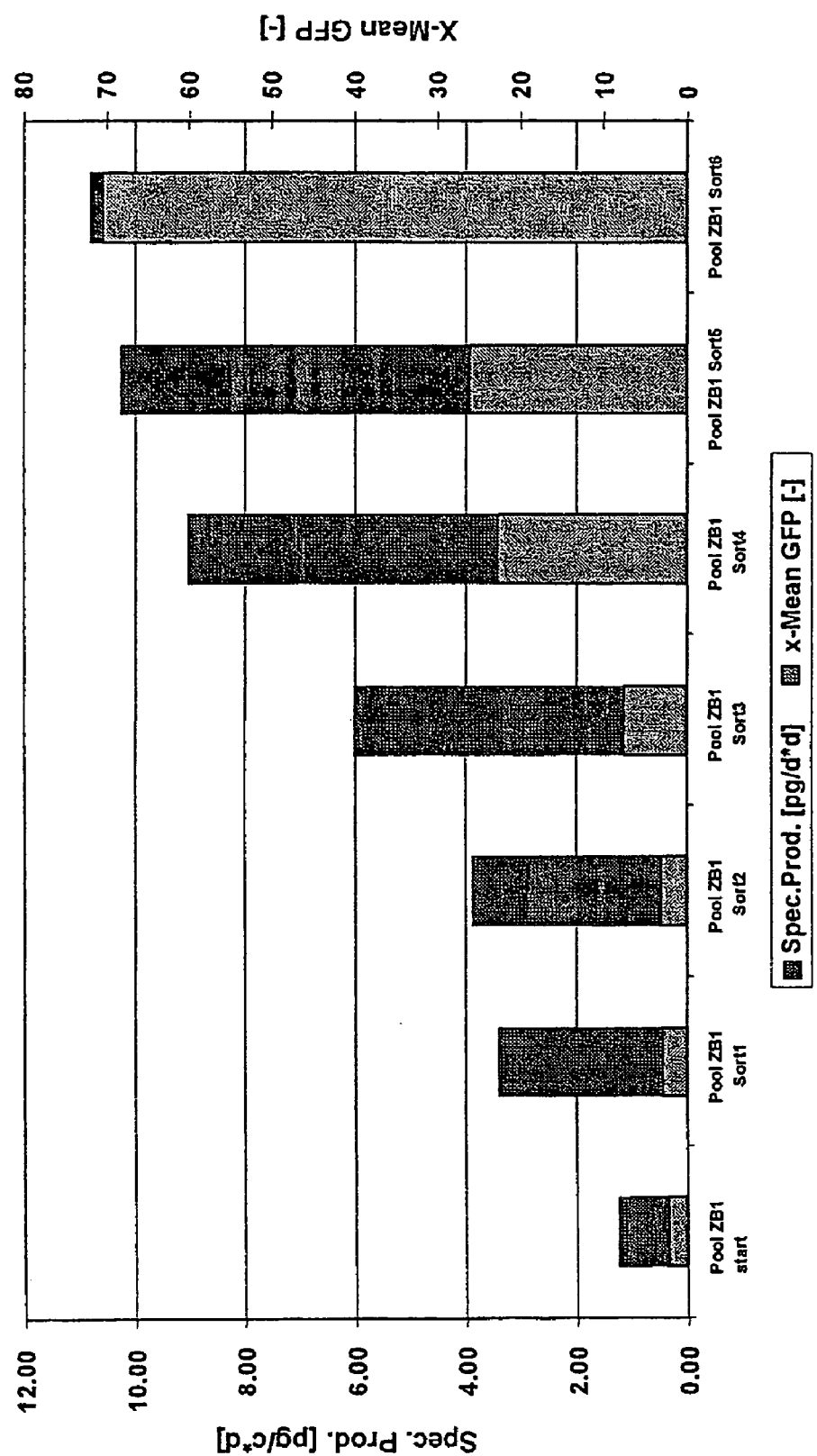

FIG. 9 shows the isolation of high expressing mAbF19 cellpools by a GFP-based selection using FACS taking the cell pool ZB1 as an example. This cell pool, which was obtained by co-transfection with the vectors pBIDG-F19HC and pBIN-F19LC (FIG. 3), was subjected to sequential GFP-based FACS sorting. The concentration of the antibody F19 in the cell culture supernatant of the pool was determined by ELISA after each sort and the specific productivity per cell and per day (pg/c/d) was calculated. Each datapoint represents the average of at least three cultivation runs.

DETAILED DESCRIPTION OF THE INVENTION AND PREFERRED EMBODIMENTS

The expression vector according to the invention contains a gene which codes for a protein of interest ("gene of interest"), functionally linked to a hamster ubiquitin/S27a promoter and a gene which codes for a fluorescent protein. Preferably, the expression vector also contains an amplifiable selectable marker gene. As used herein, "a", "an", and "the" refer to one or more entities, e.g., "a mammalian cell" refers to one or more mammalian cells.

Hamster-Ubiquitin/S27a Promoter

The ubiquitin/S27a promoter of the hamster is a powerful homologous promoter which is described in WO 97/15664. Such a promoter preferably has at least one of the following features: GC-rich sequence area, Sp1 binding site, polypyrimidine element, absence of a TATA box. Particularly preferred is a promoter which has an Sp1 binding site but no TATA box. Also preferred is a promoter which is constitutively activated and in particular is equally active under serum-containing, low-serum and serum-free cell culture conditions. In another embodiment it is an inducible promoter, particularly a promoter which is activated by the removal of serum.

A particularly advantageous embodiment is a promoter with a nucleotide sequence as contained in FIG. 5 of WO 97/15664. Particularly preferred are promoter sequences which contain the sequence from position −161 to −45 of FIG. 5.

The promoters used in the examples of the present patent specification each contain a DNA molecule with the sequence from position 1923 to 2406 of SEQ ID NO: 1 of the attached sequence listing. This sequence corresponds to the fragment −372 to +111 from FIG. 5 of WO 97/15664 and represents the preferred promoter, i.e a preferred promoter should incorporate this sequence region. Another suitable promoter fragment contains the sequence from position 2134 to 2406 (corresponding to −161 to +111 in FIG. 5 of WO 97/15664). A promoter which contains only the sequence from position 2251 to 2406 is no longer functional (corresponds to position −45 to +111 in FIG. 5 of WO 97/15664). It is possible to extend the promoter sequence in the 5' direction starting from position 2134.

It is also possible to use functional subfragments of the complete hamster ubiquitin/S27a promoter sequence as well as functional mutants/variants of the complete sequence of subfragments thereof which have been modified, for example, by substitution, insertion or deletion. Corresponding subfragments, mutants or variants are hereinafter also referred to as "modified promoters".

A modified promoter, optionally combined with other regulatory elements, preferably has a transcription activity which corresponds to that of the promoter fragment from position 1923 to 2406 of the nucleotide sequence given in SEQ ID NO:1 (−372 to +111 from FIG. 5 of WO 97/15664). A modified promoter proves to be useful for the purposes of the invention if it has a transcription activity which has at least 50%, preferably at least 80%, more preferably at least 90% and most preferably at least 100% of the activity of the 1923 to 2406 fragment (−372 to +111 fragment) in a comparative reporter gene assay. Particularly preferred are modified promoters which have a minimum sequence homology to the wild-type sequence SEQ ID NO:1 of the hamster ubiquitin/S27a promoter of at least 80%, preferably at least 85%, preferably at least 90%, more preferably at least 95% and most preferably at least 97% and have a corresponding promoter activity in a comparative reporter gene assay.

In a corresponding comparative reporter gene assay the promoter fragments to be tested including the reference sequence are cloned in front of a promoterless reporter gene which codes, for example for luciferase, secreted alkaline phosphotase or green fluorescent protein (GFP). These constructs (promoter sequence+reporter gene) are subsequently introduced into the test cells, e.g. CHO-DG44, by transfection and the induction of the reporter gene expression by the promoter fragment in question is determined by measuring the protein content of the reporter gene. A corresponding test is found for example in Ausubel et al. (Ausubel, F. M. et al., Current Protocols in molecular biology. New York: Greene Publishing Associates and Wiley-Interscience. 1994).

The promoter sequence of the hamster ubiquitin/S27a promoter and the modified promoters, which may also include, for example, the 5' untranslated region or selected fragments thereof, and the coding region of the ubiquitin/S27a gene or selected fragments thereof, may be obtained by a skilled artisan with a knowledge of the sequence described in WO 97/15664 using various standard methods (for example, Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994). Starting from the sequence described in WO 97/15664 a suitable fragment may be selected, for example, and an oligonucleotide probe containing the sequence of this fraction may be chemically synthesised. A probe of this kind may be used for example to clone the ubiquitin/S27a gene or the 5' untranslated region or other fragments thereof, for example by hybridisation from a library of the hamster genome. Using the reporter gene assay described above the skilled artisan is in a position to identify promoter-active fragments without any great effort and use them for the purposes of the present invention. The 5' untranslated region or special fragments thereof can easily be obtained by PCR amplification with corresponding primers from genomic DNA or a genomic library. Fragments of the 5' untranslated region may also be obtained by limited exonuclease III digestion from larger DNA fragments. Such DNA molecules may also be chemically synthesised or produced from chemically synthesised fragments by ligation.

Deletion, insertion and substitution mutants may be produced by "site-specific mutagenesis" and/or "PCR-based mutagenesis techniques". Corresponding methods are mentioned for example in Lottspeich and Zorbas (Lottspeich F. and Zorbas H. eds., Bioanalytic, Spektrum Akad. Verl., 1998 Chapter 36.1 with further references).

By cross-hybridisation with probes from the 5' untranslated region of the hamster ubiquitin/S27a gene or from the S27a part of the hamster ubiquitin S27a gene it is also possible to identify and isolate suitable promoter sequences from corresponding homologous genes of other, preferably mammalian species. Suitable techniques are described by way of example in Lottspeich and Zorbas (Lottspeich F. and Zorbas H. eds., Bioanalytic, Spektrum Akad. Verl., 1998, Chapter 23). Genes are "homologous" for the purposes of the invention if their nucleotide sequence exhibits at least 70%, preferably at least 80%, preferably at least 90%, more preferably at least 95% and most preferably at least 97% conformity to the nucleotide sequence of the gene with which it is homologous.

Gene of Interest

The gene of interest contained in the expression vector according to the invention comprises a nucleotide sequence of any length which codes for a product of interest. The gene product or "product of interest" is generally a protein, polypeptide, peptide or fragment or derivative thereof. However, it may also be RNA or antisense RNA. The gene of interest may be present in its full length, in shortened form, as a fusion gene or as a labelled gene. It may be genomic DNA or preferably cDNA or corresponding fragments of fusions. The gene of interest may be the native gene sequence, or it may be mutated or otherwise modified. Such modifications include codon optimisations for adapting to a particular host cell and humanisation. The gene of interest may, for example, code for a secreted, cytoplasmic, nuclear-located, membrane-bound or cell surface-bound polypeptide.

The term "nucleotide sequence" or "nucleic acid sequence" indicates an oligonucleotide, nucleotides, polynucleotides and fragments thereof as well as DNA or RNA of genomic or synthetic origin which occur as single or double strands and can represent the coding or non-coding strand of a gene. Nucleic acid sequences may be modified using standard techniques such as site-specific mutagenesis or PCR-mediated mutagenesis (e.g. described in Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994).

By "coding" or "encoding" is meant the property or capacity of a specific sequence of nucleotides in a nucleic acid, for example a gene in a chromosome or an mRNA, to act as a matrix for the synthesis of other polymers and macromolecules such as for example rRNA, tRNA, mRNA, other RNA molecules, cDNA or polypeptides in a biological process. Accordingly, a gene codes for a protein if the desired protein is produced in a cell or another biological system by transcription and subsequent translation of the mRNA. Both the coding strand whose nucleotide sequence is identical to the mRNA sequence and is normally also given in sequence databanks, e.g. EMBL or GenBank, and also the non-coding strand of a gene or cDNA which acts as the matrix for transcription may be referred to as coding for a product or protein. A nucleic acid which codes for a protein also includes nucleic acids which have a different order of nucleotide sequence on the basis of the degenerate genetic code but result in the same amino acid sequence of the protein. Nucleic acid sequences which code for proteins may also contain introns.

The term cDNA denotes deoxyribonucleic acids which are prepared by reverse transcription and synthesis of the second DNA strand from a mRNA or other RNA produced from a gene. If the cDNA is present as a double stranded DNA molecule it contains both a coding and a non-coding strand.

The term intron denotes non-coding nucleotide sequences of any length. They occur naturally in numerous eukaryotic genes and are eliminated from a previously transcribed mRNA precursor by a process known as splicing. This requires precise excision of the intron at the 5' and 3' ends and correct joining of the resulting mRNA ends so as to produce a mature processed mRNA with the correct reading frame for successful protein synthesis. Many of the splice donor and splice acceptor sites involved in this splicing process, i.e. the sequences located directly at the exon-intron or intron-exon interfaces, have been characterised. For an overview see Ohshima et al. (Ohshima,Y. et al., J Mol Biol 1987,195, 247-259).

Protein/Product of Interest

Proteins/polypeptides with a biopharmaceutical significance include for example antibodies, enzymes, cytokines, lymphokines, adhesion molecules, receptors and the derivatives or fragments thereof, but are not restricted thereto. Generally, all polypeptides which act as agonists or antagonists and/or have therapeutic or diagnostic applications are of value.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitution, deletion or insertion of amino acids and fusion with other proteins while retaining its biological activity.

Examples of therapeutic proteins are insulin, insulin-like growth factor, human growth hormone (hGH) and other growth factors, tissue plasminogen activator (tPA), erythropoietin (EPO), cytokines, e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18 interferon (IFN)-alpha, -beta, -gamma, -omega or -tau, tumour necrosis factor (TNF) such as TNF-alpha, beta or gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')$_2$, Fc and Fc' fragments, light (L) and heavy (H) immunoglobulin chains and the constant, variable or hypervariable regions thereof as well as Fv and Fd fragments (Chamov, S. M. et al., Antibody Fusion Proteins, Wiley-Liss Inc., 1999). The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')$_2$ fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable =fragment of the variable part). As covalent binding via the cystein groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described (cf. for example Huston, C. et al., *Proc Natl Acad Sci USA* 1988, 85 (16), 5879-5883).

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the leucine zipper domains. In other strategies the interactions between the VH and VL regions of the scFv fragment are used for multimerisation (e.g. dia-, tri- and pentabodies).

The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphide bridges. Examples of diabodies can be found in the literature, e.g. in Perisic et al. (Perisic, O. et al., *Structure* 1994, 2, 1217-1226).

The term minibody is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region. Examples of such minibodies are described by Hu et al. (Hu, S. et al., Cancer Res. 1996, 56 (13), 3055-3061).

The term triabody is used in the art to denote a trivalent homotrimeric scFv derivative (Kortt, A. A. et al., *Protein Engineering* 1997, 10 (4), 423-433). The direct fusion of VH VL without the use of a linker sequence leads to the formation of trimers.

The fragments known in the art as mini antibodies which have a bi-, tri- or tetravalent structure are also derivatives of scFv fragments. The multimerisation is achieved by means of di-, tri- or tetrameric coiled coil structures (Pack, P. et al., *Biotechnology* 1993, 11, 1271-1277; Pack, P. et al., *J Mol Biol* 1995, 246 (11), 28-34; Lovejoy, B. et al., *Science* 1993, 259, 1288-1293).

Gene Which Codes for a Fluorescent Protein

The expression vector according to the invention contains a gene coding for a fluorescent protein functionally linked to the gene of interest and under the control of the hamster-ubiquitin/S27a promoter, a modified hamster-ubiquitin/S27a promoter or a homologue thereof.

The fluorescent protein may be, for example, a green, bluish-green, blue, yellow or other coloured fluorescent protein. One particular example is green fluorescent protein (GFP) obtained from *Aequorea victoria* or *Renilla reniformis* and mutants developed from them (cf. for example Bennett, R. P. et al., BioTechniques 1998, 24, 478-482; Chalfie, M. et al., Science 1994, 263, 802-805; WO 01/04306 and the literature cited therein).

Other fluorescent proteins and genes coding for them are described in WO 00/34318, WO 00/34326, WO 00/34526 and WO 01/27150 which are incorporated herein by reference. These fluorescent proteins are fluorophores of non-bioluminescent organisms of the species Anthozoa, for example *Anemonia majano*, *Clavularia* sp., *Zoanthus* sp. I, *Zoanthus* sp. II, *Discosoma striata*, *Discosoma* sp. "red", *Discosoma* sp. "green", *Discosoma* sp. "Magenta", *Anemonia sulcata*.

The fluorescent proteins used according to the invention contain in addition to the wild-type proteins natural or genetically engineered mutants and variants, fragments, derivatives or variants thereof which have for example been fused with other proteins or peptides. The mutations used may for example alter the excitation or emission spectrum, the formation of chromophores, the extinction coefficient or the stability of the protein. Moreover, the expression in mammalian cells or other species can be improved by codon optimisation. According to the invention the fluorescent protein may also be used in fusion with a selectable marker, preferably an amplifiable selectable marker such as dihydrofolate reductase (DHFR).

The fluorescence emitted by the fluorescent proteins makes it possible to detect the proteins, e.g. by throughflow cytometry with a fluorescence-activated cell sorter (FACS) or by fluorescence microscopy.

Other Regulatory Elements

The hamster-ubiquitin/S27a promoter may be functionally combined with other regulatory sequences in order to increase/regulate the transcription activity in an expression cassette.

For example, the promoter may be functionally linked to enhancer sequences in order to increase the transcriptional activity. For this, one or more enhancers and/or several copies of an enhancer sequence may be used, e.g. a CMV or SV40 enhancer.

The term enhancer denotes a polynucleotide sequence which in the cis location acts on the activity of a promoter and thus stimulates the transcription of a gene functionally connected to this promoter. Unlike promoters the effect of enhancers is independent of position and orientation and they can therefore be positioned in front of or behind a transcription unit, within an intron or even within the coding region. The enhancer may be located both in the immediate vicinity of the transcription unit and at a considerable distance from the promoter. It is also possible to have a physical and functional overlap with the promoter. The skilled artisan will be aware of a number of enhancers from various sources (and deposited in databanks such as GenBank, e.g. SV40 enhancers, CMV enhancers, polyoma enhancers, adenovirus enhancers) which are available as independent elements or elements cloned within polynucleotide sequences (e.g. deposited at the ATCC or from commercial and individual sources). A number of promoter sequences also contain enhancer sequences such as the frequently used CMV promoter. The human CMV enhancer is one of the strongest enhancers identified hitherto. One example of an inducible enhancer is the metallothionein enhancer, which can be stimulated by glucocorticoids or heavy metals.

Another possible modification is, for example, the introduction of multiple Sp1 binding sites. The promoter sequences may also be combined with regulatory sequences which allow control/regulation of the transcription activity. Thus, the promoter can be made repressible/ inducible. This can be done for example by linking to sequences which are binding sites for up- or down-regulating transcription factors. The above-mentioned transcription factor Sp1, for example, has a positive effect on the transcription activity. Another example is the binding site for the activator protein AP1, which may act both positively and negatively on transcription. The activity of AP1 can be controlled by all kinds of factors such as, for example, growth factors, cytokines and serum (Faisst, S. et al., *Nucleic Acids Research* 1992, 20, 3-26 and references therein). The transcription efficiency can also be increased by changing the promoter sequence by the mutation (substitution, insertion or deletion) of one, two, three or more bases and then determining, in a reporter gene assay, whether this has increased the promoter activity.

Basically, the additional regulatory elements include promoters other than the hamster-ubiquitin/S27a promoter, enhancers, termination and polyadenylation signals and other expression control elements. Both inducible and constitutively regulatory sequences are known for the various cell types. "Transcription-regulatory elements" generally comprise a promoter upstream of the gene sequence to be expressed, transcription initiation and termination sites and a polyadenylation signal.

The term promoter denotes a polynucleotide sequence which allows and controls the transcription of the genes or sequences functionally connected therewith. A promoter contains recognition sequences for binding RNA polymerase and the initiation site for transcription (transcription initiation site). In order to express a desired sequence in a certain cell type or a host cell a suitable functional promoter must be chosen. The skilled artisan will be familiar with a variety of promoters from various sources, including constitutive, inducible and repressible promoters. Promoters are deposited in databanks such as GenBank, for example, and may be obtained as separate elements or elements cloned within polynucleotide sequences from commercial or individual sources. In inducible promoters the activity of the promoter may be reduced or increased in response to a signal. One example of an inducible promoter is the tetracycline (tet) promoter. The tet promoter contains tetracycline operator sequences (tetO) which can be induced by a tetracycline-regulated transactivator protein (tTA). In the presence of tetracycline, the binding of tTA to tetO is inhibited. Examples of other inducible promoters are the jun, fos, metallothionein and heat shock promoter (see also Sambrook, J. et al., Molecular Cloning: A Laboratory Manual Cold Spring Harbor Laboratory, Cold Spring Harbor, N.Y., 1989; Gossen, M. et al., *Curr Opinions Biotech* 1994, 5, 516-520). Of the promoters which are particularly suitable for high expression in eukaryotes, there are for example the SV40 early promoter, adenovirus major late promoter, mouse metallothionein-l promoter, the long terminal repeat region of Rous Sarcoma Virus and the early promoter of human Cytomegalovirus. Examples of other heterologous mammalian promoters are the actin, immunoglobulin or heat shock promoter(s).

The term "transcription initiation site" refers to a nucleic acid in the construct which corresponds to the first nucleic acid which is incorporated in the primary transcript, i.e. the mRNA precursor. The transcription initiation site may overlap with the promoter sequences.

The term "transcription termination site" refers to a nucleotide sequence which is normally at the 3' end of the gene of interest or of the gene section which is to be transcribed, and which brings about the termination of transcription by RNA polymerase.

The "polyadenylation signal" is a signal sequence which causes cleavage at a specific site at the 3' end of the eukaryotic mRNA and post-transcriptional incorporation of a sequence of about 100-200 adenine nucleotides (polyA tail) at the cleaved 3' end. The polyadenylation signal comprises the sequence AATAAA about 10-30 nucleotides upstream of the cleavage site and a sequence located downstream. Various polyadenylation elements are known such as tk polyA, SV40 late and early polyA or BGH polyA (described for example in U.S. Pat. No. 5,122,458).

In a preferred embodiment of the present invention each transcription unit has a promoter or a promoter/enhancer element, a gene of interest and/or a marker gene as well as a transcription termination element. In another preferred embodiment the transcription unit contains two further translation regulatory units.

"Translation regulatory elements" comprise a translation initiation site (AUG), a stop codon and a polyA signal for each polypeptide to be expressed. For optimum expression it may be advisable to remove, add or change 5'- and/or 3'-untranslated regions of the nucleic acid sequence which is to be expressed, in order to eliminate any potentially unsuitable additional translation initiation codons or other sequences which might affect expression at the transcription or expression level. In order to promote expression, ribosomal consensus binding sites may alternatively be inserted immediately upstream of the start codon. In order to produce a secreted polypeptide the gene of interest usually contains a signal sequence which codes for a signal precursor peptide which transports the synthesised polypeptide to and through the ER membrane. The signal sequence is often but not always located at the amino terminus of the secreted protein and is cleaved by signal peptidases after the protein has been inserted through the ER membrane. The gene sequence will usually but not necessarily contain its own signal sequence. If the native signal sequence is not present a heterologous signal sequence may be introduced in known manner. Numerous signal sequences of this kind are known to the skilled artisan and deposited in sequence databanks such as GenBank and EMBL.

One important regulatory element according to the invention is the internal ribosomal entry site (IRES). The IRES element comprises a sequence which functionally activates the translation initiation independently of a 5'-terminal methylguanosinium cap (CAP structure) upstream of the gene and in an animal cell allows the translation of two cistrons (open reading frames) from a single transcript. The IRES element provides an independent ribosomal entry site for the translation of the open reading frame located immediately downstream. In contrast to bacterial mRNA which may be multicistronic, i.e. it may code for numerous different polypeptides or products which are translated one after the other by the mRNA, the majority of mRNAs from animal cells are monocistronic and code for only one protein or product. In the case of a multicistronic transcript in a eukaryotic cell the translation would be initiated from the translation initiation site which was closest upstream and would be stopped by the first stop codon, after which the transcript would be released from the ribosome. Thus, only the first polypeptide or product coded by the mRNA would be produced during translation. By contrast, a multicistronic transcript with an IRES element which is functionally linked to the second or subsequent open reading frame in the transcript allows subsequent translation of the open reading frame located downstream thereof, so that two or more polypeptides or products coded by the same transcript are produced in the eukaryotic cell.

The IRES element may be of various lengths and various origins and may originate, for example, from the encephalomyocarditis virus (EMCV) or other Picorna viruses. Various IRES sequences and their use in the construction of vectors are described in the literature (cf. for example Pelletier, J. et al., *Nature* 35 1988, 334, 320-325; Jang, S. K. et al., *J Virol* 1989, 63, 1651-1660; Jang, S. K. et al., *J Virol* 1989, 63, 1651-1660; Adam, M. A. et al., *J Virol* 1991, 65, 4985-4990; Morgan, R. A. et al., *Nucleic Acids Research* 1992, 20, 1293-1299; Sugimoto et al., *Biotechnology* 1994, 12, 694-698; Ramesh, N. et al., *Nucleic Acids Research* 1996, 24, 2697-2700; Mosser, D. D. et al., *BioTechniques* 1997, 22,150-161).

The gene sequence located downstream is functionally linked to the 3' end of the IRES element, i.e. the spacing is selected so that the expression of the gene is unaffected or only marginally affected or has sufficient expression for the intended purpose. The optimum permissible distance between the IRES element and the start codon of the gene located downstream thereof for sufficient expression can be determined by simple experiments by varying the spacing and determining the expression rate as a function of the spacing using reporter gene assays.

By the measures described it is possible to obtain an optimum expression cassette which is of great value for the expression of heterologous gene products. An expression cassette obtained by means of one or more such measures is therefore a further subject of the invention.

Amplifiable Selectable Marker Gene

A preferred vector according to the invention additionally contains an amplifiable selectable marker gene which allows amplification of the amplifiable marker gene and preferably co-amplification of a transcription unit consisting of the hamster-ubiquitin/S27a gene, the gene of interest and the gene for the fluorescent protein. For this, the host cells transfected with a corresponding expression vector are cultivated in the presence of a suitable selection agent, so that only those host cells which have a number of gene copies of at least the amplifiable selectable marker gene can replicate. Preferably, this is achieved by stepwise cultivation of the cells in the presence of increasing amounts of selecting agent.

The amplifiable selectable marker gene usually codes for an enzyme which is needed for the growth of eukaryotic cells under certain cultivation conditions. For example, the amplifiable selectable marker gene may code for dihydrofolate reductase (DHFR). In this case the gene is amplified if a host cell transfected therewith is cultivated in the presence of the selecting agent methotrexate (MTX).

The following Table 1 gives examples of other amplifiable selectable marker genes and the associated selecting agents which may be used according to the invention, which are described in an overview by Kaufman (Kaufman, R. J. Methods in Enzymology, 185:537-566,1990).

TABLE 1

Amplifiable selectable marker genes

| Amplifiable selectable marker gene | Accession number | Selecting agent |
|---|---|---|
| dihydrofolate reductase | M19869 (hamster) E00236 (mouse) | methotrexate (MTX) |
| metallothionein | D10551 (hamster) M13003 (human) M11794 (rat) | cadmium |
| CAD (carbamoylphosphate synthetase: aspartate transcarbamylase: dihydroorotase) | M23652 (hamster) D78586 (human) | N-phosphoacetyl-L-aspartate |
| adenosine-deaminase | K02567 (human) M10319 (mouse) | Xyl-A- or adenosine, 2'deoxycoformycin |
| AMP (adenylate)-deaminase | D12775 (human) J02811 (rat) | adenine, azaserin, coformycin |
| UMP-synthase | J03626 (human) | 6-azauridine, pyrazofuran |
| IMP 5'-dehydrogenase | J04209 (hamster) J04208 (human) M33934 (mouse) | mycophenolic acid |
| xanthine-guanin-phosphoribosyltransferase | X00221 (E. coli) | mycophenolic acid with limiting xanthine |
| mutant HGPRTase or mutant thymidine-kinase | J00060 (hamster) M13542, K02581 (human) J00423, M68489(mouse) M63983 (rat) M36160 (Herpes virus) | hypoxanthine, aminopterine and thymidine (HAT) |
| thymidylate-synthetase | D00596 (human) M13019 (mouse) L12138 (rat) | 5-fluorodeoxyuridine |
| P-glycoprotein 170 (MDR1) | AF016535 (human) J03398 (mouse) | several drugs, e.g. adriamycin, vincristin, colchicine |

TABLE 1-continued

Amplifiable selectable marker genes

| Amplifiable selectable marker gene | Accession number | Selecting agent |
|---|---|---|
| ribonucleotide reductase | M124223, K02927 (mouse) | aphidicoline |
| glutamine-synthetase | AF150961 (hamster) U09114, M60803 (mouse) M29579 (rat) | methionine sulphoximine (MSX) |
| asparagine-synthetase | M27838 (hamster) M27396 (human) U38940 (mouse) U07202 (rat) | β-aspartylhydroxamate, albizziin, 5'azacytidine |
| argininosuccinate-synthetase | X01630 (human) M31690 (mouse) M26198 (bovine) | canavanin |
| ornithine-decarboxylase | M34158 (human) J03733 (mouse) M16982 (rat) | α-difluoromethylornithine |
| HMG-CoA-reductase | L00183, M12705 (hamster) M11058 (human) | compactin |
| N-acetylglucosaminyl-transferase | M55621 (human) | tunicamycin |
| threonyl-tRNA-synthetase | M63180 (human) | borrelidin |
| Na⁺K⁺-ATPase | J05096 (human) M14511 (rat) | ouabain |

According to the invention the amplifiable selectable marker gene used is preferably a gene which codes for a polypeptide with the function of DHFR, e.g. for DHFR or a fusion protein from the fluorescent protein and DHFR. DHFR is necessary for the biosynthesis of purines. Cells which lack the DHFR genes cannot grow in purine-deficient medium. The DHFR gene is therefore a useful selectable marker for selecting and amplifying genes in cells cultivated in purine-free medium. The selecting medium used in conjunction with the DHFR gene is methotrexate (MTX). The present invention therefore includes a method of preparing highly productive recombinant host cells which contains the following steps: (i) transfection of the host cells with genes which code at least for a protein of interest, a fluorescent protein and DHFR; (ii) cultivation of the cells under conditions which allow expression of the various genes, and (iii) the amplification of the co-integrated genes by cultivating the cells in the presence of a selecting agent which allows the amplification of at least the amplifiable selectable marker gene such as methotrexate. Preferably the transfected cells are cultivated in hypoxanthine/thymidine-free medium in the absence of serum and with the addition of increasing concentrations of MTX. Preferably the concentration of MTX in the first amplification step is at least 200 nM and in a more preferred embodiment it is at least 500 nM and may be increased step by step to 1 μM. In individual cases concentrations of more than 1 μM may be used.

Mammalian cells, preferably mouse myeloma and hamster cells, are preferred host cells for the use of DHFR as an amplifiable selectable marker. The cell lines CHO-DUKX (ATCC CRL-9096) and CHO-GD44 (Urlaub, G. et al., Cell 1983, 33, 405-412) are particularly preferred as they have no DHFR activity of their own, as a result of mutation. In order to be able to use the DHFR-induced amplification in other cell types as well which have their own endogenous DHFR activity, it is possible to use in the transfection process a mutated DHFR gene which codes for a protein with reduced sensitivity to methotrexate (Simonson, C. C. et al., *Proc Natl Acad Sci USA* 1983, 80, 2495-2499; Wigler, M. et al., *Proc Natl Acad Sci USA* 1980, 77, 3567-3570; Haber, D. A. et al., *Somatic Cell Genetics* 1982, 8, 499-508).

Preparation of Expression Vectors According to the Invention

The expression vector according to the invention may theoretically be prepared by conventional methods known in the art, as described by Sambrook et al. (Sambrook, J. et al., Molecular Cloning: A Laboratory Manual Cold Spring Harbor Laboratory, Cold Spring Harbor, N.Y., 1989), for example. Sambrook also describes the functional components of a vector, e.g. suitable promoters (in addition to the hamster ubiquitin/S27a promoter), enhancers, termination and polyadenylation signals, antibiotic resistance genes, selectable markers, replication starting points and splicing signals. Conventional cloning vectors may be used to produce them, e.g. plasmids, bacteriophages, phagemids, cosmids or viral vectors such as baculovirus, retroviruses, adenoviruses, adeno-associated viruses and herpes simplex virus, as well as artificial chromosomes/mini chromosomes. The eukaryotic expression vectors typically also contain prokaryotic sequences such as, for example, replication origin and antibiotic resistance genes which allow replication and selection of the vector in bacteria. A number of eukaryotic expression vectors which contain multiple cloning sites for the introduction of a polynucleotide sequence are known and some may be obtained commercially from various companies such as Stratagene, La Jolla, Calif., USA; Invitrogen, Carlsbad, Calif., USA; Promega, Madison, Wis., USA or BD Biosciences Clontech, Palo Alto, Calif., USA.

The hamster-ubiquitin/S27a promoter, the gene of interest, the gene coding for a fluorescent protein and preferably also the amplifiable selectable marker gene, e.g. dihydrofolate reductase, and optionally additional regulatory elements such as the internal ribosomal entry site (IRES), enhancers or a polyadenylation signal are introduced into the expression vector in a manner familiar to those skilled in the art. An expression vector according to the invention contains, at the minimum, a ubiquitin/S27a promoter, the gene of interest and the gene coding for a fluorescent protein. Preferably, the expression vector also contains an amplifiable selectable marker gene. According to the invention, modified ubiquitin/S27a promoters, e.g. the modified ubiquitin/S27a promoters described in the present application, are also used. Particularly preferred is an expression vector in which the ubiquitin promoter, the gene of interest and the gene which codes for a fluorescent protein are functionally linked together or are functionally linked.

Within the scope of the present description the term "functional linking" or "functionally linked" refers to two or more nucleic acid sequences or partial sequences which are positioned so that they can perform their intended function.

For example, a promoter/enhancer is functionally linked to a coding gene sequence if it is able to control or modulate the transcription of the linked gene sequence in the cis position. Generally, but not necessarily, functionally linked DNA sequences are close together and, if two coding gene sequences are linked or in the case of a secretion signal sequence, in the same reading frame. Although a functionally linked promoter is generally located upstream of the coding gene sequence it does not necessarily have to be close to it. Enhancers need not be close by either, provided that they assist the transcription of the gene sequence. For this purpose they may be both upstream and downstream of the gene sequence, possibly at some distance from it. A polyadenylation site is functionally linked to a gene sequence if it is positioned at the 3' end of the gene sequence in such a way that the transcription progresses via the coding sequence to the polyadenylation signal. Linking may take place according to conventional recombinant methods, e.g. by the PCR technique, by ligation at suitable restriction cutting sites or by splicing. If no suitable restriction cutting sites are available synthetic oligonucleotide linkers or adaptors per se may be used in a manner known. According to the invention the functional linking preferably does not take place via intron sequences.

In one of the embodiments described, the ubiquitin/S27a promoter or a modified form thereof, the gene of interest and the gene coding for a fluorescent protein are functionally linked together. This means for example that both the gene of interest and the gene coding for a fluorescent protein are expressed starting from the same ubiquitin/S27a promoter or a modified form thereof. In a particularly preferred embodiment the functional linking takes place via an IRES element, so that a bicistronic mRNA is synthesised from both genes. The expression vector according to the invention may additionally contain enhancer elements which act functionally on one or more promoters. Particularly preferred is an expression vector in which the ubiquitin/S27a promoter or a modified form thereof is linked to an enhancer element, e.g. an SV40 enhancer or a CMV enhancer element.

Fundamentally, the expression of the genes within an expression vector may take place starting from one or more transcription units. The term transcription unit is defined as a region which contains one or more genes to be transcribed. The genes within a transcription unit are functionally linked to one another in such a way that all the genes within such a unit are under the transcriptional control of the same promoter or promoter/ enhancer. As a result of this transcriptional linking of genes, more than one protein or product can be transcribed from a transcription unit and thus expressed. Each transcription unit contains the regulatory elements which are necessary for the transcription and translation of the gene sequences contained therein. Each transcription unit may contain the same or different regulatory elements. IRES elements or introns may be used for the functional linking of the genes within a transcription unit.

The expression vector may contain a single transcription unit for expressing the gene of interest, the gene for the fluorescent protein and the amplifiable selectable marker. Alternatively, these genes may also be arranged in two or more transcription units. Various combinations of the genes within a transcription unit are possible. In another embodiment of the present invention more than one expression vector consisting of one, two or more transcription units may be inserted in a host cell by cotransfection or in successive transfections in any desired order. Any combination of regulatory elements and genes on each vector can be selected provided that adequate expression of the transcription units is ensured. If necessary, other regulatory elements and genes, e.g. additional genes of interest or selectable markers, may be positioned on the expression vectors.

Accordingly, the expression vector according to the invention may contain the gene which codes for a fluorescent protein and the amplifiable selectable marker gene in one or in two separate transcription units. Each transcription unit can transcribe and express one or more gene products. If both genes are contained in one transcription unit they are under the control of the same promoter or promoter/enhancer, while preferably an IRES element is used to ensure the functional linking of all the components. If the gene which codes for a fluorescent protein and the amplifiable selectable marker gene are contained in two separate transcription units, they may be under the control of the same or different promoters/enhancers. However, preferably, its natural or a weaker heterologous promoter, e.g. SV40 early promoter, is used for the selectable marker gene and preferably no enhancer is used. Expression vectors with two separate transcription units are preferred within the scope of the invention. One (bicistronic) transcription unit contains the gene of interest and the gene coding for a fluorescent protein, while the other transcription unit contains the amplifiable selectable marker gene. Preferably, each transcription unit is limited at the 3' end by a sequence which codes for a polyA signal, preferably tk polyA, BGH polyA or SV40 polyA.

Also preferred according to the invention are those vectors which instead of the gene of interest have only a multiple cloning site which allows the cloning of the gene of interest via recognition sequences for restriction endonucleases. Numerous recognition sequences for all kinds of restriction endonucleases as well as the associated restriction endonucleases are known from the prior art. Preferably, sequences are used which consist of at least six nucleotides as recognition sequence. A list of suitable recognition sequences can be found for example in Sambrook et al. (Sambrook, J. et al., Molecular Cloning: A Laboratory Manual Cold Spring Harbor Laboratory, Cold Spring Harbor, N.Y., 1989).

Host Cells

For transfection with the expression vector according to the invention eukaryotic host cells are used, preferably mammalian cells and more particularly rodent cells such as mouse, rat and hamster cell lines. The successful transfection of the corresponding cells with an expression vector according to the invention results in transformed, genetically modified, recombinant or transgenic cells, which are also the subject of the present invention.

Preferred host cells for the purposes of the invention are hamster cells such as BHK21, BHK TK⁻, CHO, CHO-K1, CHO-DUKX, CHO-DUKX B1 and CHO-DG44 cells or derivatives/descendants of these cell lines. Particularly preferred are CHO-DG44, CHO-DUKX, CHO-K1 and BHK21 cells, particularly CHO-DG44 and CHO-DUKX cells. Also suitable are myeloma cells from the mouse, preferably NS0 and Sp2/0 cells and derivatives/descendants of these cell lines.

Examples of hamster and mouse cells which can be used according to the invention are given in Table 2 that follows. However, derivatives and descendants of these cells, other mammalian cells including but not restricted to cell lines of humans, mice, rats, monkeys, rodents, or eukaryotic cells, including but not restricted to yeast, insect and plant cells, may also be used as host cells for the production of biopharmaceutical proteins.

TABLE 2

Hamster and Mouse Production Cell Lines

| Cell line | Accession Number |
| --- | --- |
| NS0 | ECASS No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21-derivative) | ATCC CRL-8544 |
| CHO | ECACC No. 8505302 |
| CHO-K1 | ATCC CCL-61 |
| CHO-DUKX (=CHO duk⁻, CHO/dhfr⁻) | ATCC CRL-9096 |

TABLE 2-continued

Hamster and Mouse Production Cell Lines

| Cell line | Accession Number |
| --- | --- |
| CHO-DUKX B1 | ATCC CRL-9010 |
| CHO-DG44 | Urlaub et al., Cell 32[2], 405-412, 1983 |
| CHO Pro-5 | ATCC CRL-1781 |
| V79 | ATCC CCC-93 |
| B14AF28-G3 | ATCC CCL-14 |
| CHL | ECACC No. 87111906 |

The transfection of the eukaryotic host cells with a polynucleotide or one of the expression vectors according to the invention is carried out by conventional methods (Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994). Suitable methods of transfection include for example liposome-mediated transfection, calcium phosphate co-precipitation, electroporation, polycation- (e.g. DEAE dextran)-mediated transfection, protoplast fusion, microinjection and viral infections. According to the invention stable transfection is preferably carried out in which the constructs are either integrated into the genome of the host cell or an artificial chromosome/minichromosome, or are episomally contained in stable manner in the host cell. The transfection method which gives the optimum transfection frequency and expression of the heterologous gene in the host cell in question is preferred. By definition, every sequence or every gene inserted in a host cell is referred to as a "heterologous sequence" or "heterologous gene" in relation to the host cell. This applies even if the sequence to be introduced or the gene to be introduced is identical to an endogenous sequence or an endogenous gene of the host cell. For example, a hamster actin gene introduced into a hamster host cell is by definition a heterologous gene.

In the recombinant production of heterodimeric proteins such as e.g. monoclonal antibodies (mAb), the transfection of suitable host cells can theoretical be carried out by two different methods. Monoclonal antibodies of this kind are composed of a number of subunits, the heavy and light chains. Genes coding for these subunits may be accommodated in independent or multicistronic transcription units on a single plasmid with which the host cell is then transfected. This is intended to secure the stoichiometric representation of the genes after integration into the genome of the host cell. However, in the case of independent transcriptional units it must hereby be ensured that the mRNAs which encode the different proteins display the same stability and transcriptional and translational efficiency. In the second case, the expression of the genes take place within a multicistronic transcription unit by means of a single promoter and only one transcript is formed. By using IRES elements, a highly efficient internal translation initiation of the genes is obtained in the second and subsequent cistrons. However, the expression rates for these cistrons are lower than that of the first cistron, the translation initiation of which, by means of a so-called "cap"-dependent pre-initiation complex, is substantially more efficient than IRES-dependent translation initiation. In order to achieve a truly equimolar expression of the cistrons, additional intercistronic elements may be introduced, for example, which ensure uniform expression rates in conjunction with the IRES elements (WO 94/05785).

Another possible way of simultaneously producing a number of heterologous, proteins, which is preferred according to the invention, is cotransfection, in which the genes are separately integrated in different expression vectors. Co-transfection has the advantage that certain proportions of genes and gene products with one another can be adjusted, thereby balancing out any differences in the mRNA stability and in the efficiency of transcription and translation. In addition, the expression vectors are more stable because of their small size and are easier to handle both during cloning and during transfection.

In one particular embodiment of the invention, therefore, the host cells are additionally transfected, preferably co-transfected, with one or more vectors having genes which code for one or more other proteins of interest. The other vector or vectors used for the cotransfection code, for example, for the other protein or proteins of interest under the control of the same promoter/enhancer combination and for at least one other selectable marker, for example neomycin phosphotransferase.

According to the invention the host cells are preferably established, adapted and cultivated under serum-free conditions, optionally in media which are free from animal proteins/peptides. Examples of commercially obtainable media include Ham's F12 (Sigma, Deisenhofen, Del.), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S-SFMII (Invitrogen), serum-free CHO-Medium (Sigma) and protein-free CHO-Medium (Sigma). Each of these media may optionally be supplemented with various compounds, e.g. hormones and/or other growth factors (e.g. insulin, transferrin, epidermal growth factor, insulin-like growth factor), salts (e.g. sodium chloride, calcium, magnesium, phosphate), buffers (e.g. HEPES), nucleosides (e.g. adenosine, thymidine), glutamine, glucose or other equivalent nutrients, antibiotics and/or trace elements. Although serum-free media are preferred according to the invention, the host cells may also be cultivated using media which have been mixed with a suitable amount of serum. In order to select genetically modified cells which express one or more selectable marker genes, one or more selecting agents are added to the medium.

The term "selecting agent" refers to a substance which affects the growth or survival of host cells with a deficiency for the selectable marker gene in question. For example, in order to select for the presence of an expressed antibiotic resistance gene such as neomycin phosphotransferase, the antibiotic geneticin (G418) is preferably used as the medium additive. The selecting agent may also be a substance which triggers amplification of the selectable marker gene if the gene used is an amplifiable selectable marker gene (cf. Table 1). Methotrexate, for example, is a selecting medium which is suitable for amplifying the DHFR gene. Examples of other selecting agents which trigger amplification are listed in Table 1.

A selectable marker gene is a gene which allows the specific selection of cells which contain this gene by the addition of a corresponding selecting agent to the cultivation medium. As an illustration, an antibiotic resistance gene may be used as a positive selectable marker. Only cells which have been transformed with this gene are able to grow in the presence of the corresponding antibiotic and are thus selected. Untransformed cells, on the other hand, are unable to grow or survive under these selection conditions. There are positive, negative and bifunctional selectable markers. Positive selectable markers permit the selection and hence enrichment of transformed cells by conferring resistance to the selecting agent or by compensating for a metabolic or catabolic defect in the host cell. By contrast, cells which have received the gene for the selectable marker can be selectively eliminated by negative selectable markers. An example of this is the thymidine kinase gene of the Herpes Simplex virus, the expression of which in cells with the simultaneous addition of acyclovir or gancyclovir leads to the elimination thereof. The selectable markers used in this invention, including the amplifiable selectable markers, include genetically modified mutants and variants, fragments, functional equivalence, derivatives, homologues and fusions with other proteins or peptides, provided that the selectable marker retains its selective qualities. Such derivatives display considerable homology in the amino acid sequence in the regions or domains which are deemed to be selective. The literature describes a large number of selectable marker genes including bifunctional (positive/negative) markers (see for example WO 92/08796 and WO 94/28143). Examples of selectable markers which are usually used in eukaryotic cells include the genes for aminoglycoside phosphotransferase (APH), hygromycine phosphotransferase (HYG), dihydrofolate reductase (DHFR), thymidine kinase (TK), glutamine synthetase, asparagine synthetase and genes which confer resistance to neomycin (G418), puromycin, histidinol D, belomycin, phleomycin and zeocin.

It is also possible to select transformed cells by fluorescence-activated cell sorting (FACS). For this, bacterial β-galactosidase, cell surface markers or fluorescent proteins may be used (e.g. green fluorescent protein (GFP) and the variants thereof from *Aequorea victoria* and *Renilla reniformis* or other species, red fluorescent protein and proteins which fluoresce in other colours and their variants from non-bioluminescent organisms such as e.g. *Discosoma* sp., *Anemonia* sp., *Clavularia* sp., *Zoanthus* sp.) for the selection of transformed cells.

In the present invention, the use of the DHFR gene is preferred for the selection of genetically modified (recombinant) host cells as the amplifiable selectable marker gene. This marker is particularly suitable for the selection and subsequent amplification when using DHFR negative basic cells such as CHO-DG44 or CHO-DUKX, as these cells do not express endogenous DHFR and therefore do not grow in purine-free medium. Consequently, the DHFR gene may be used here as a dominant selectable marker and the transformed cells are selected in hypoxanthine/thymidine-free medium. In order to achieve DHFR-mediate gene amplification methotrexate (MTX) is used. The growth properties are critically influenced by the addition of MTX. Usually, a substantial deterioration is observed in the fermentation robustness of the cells as the MTX concentration and amplification step increase. Surprisingly, however, it has been found that, using the clone selection system according to the invention, recombinant host cells can be enriched which display much more robust behaviour in the presence of high concentrations of MTX (cf FIG. 7). Thus, host cells which have been identified and sorted using a Fluorescence-Activated Cell Sorter (FACS) were able to be cultivated and amplified in the presence of 500 nM, preferably in the presence of 1 μM MTX, which resulted in a significant increase in productivity. Thus, a method of selecting highly productive host cells is regarded as being particularly according to the invention if host cells which are transfected with an expression vector according to the invention and express at least the gene of interest, the fluorescent protein and a DHFR gene are sorted by FACS sorting, and are subjected to a gene amplification step in the presence of at least 500 nM, preferably 1 μM of MTX.

By "fermentation robustness" is meant the growth properties of the cells, such as for example the maintenance of certain growth rates, robustness to "upscaling" (larger sizes of bioreactors) and the achievement of high cell counts and vitalities in the maintenance of the stock in order to meet the industrial production rates on upscaling.

Expression

The term expression relates to the transcription and/or translation of a heterologous gene sequence in a host cell. The expression rate can be generally determined, either on the basis of the quantity of corresponding mRNA which is present in the host cell or on the basis of the quantity of gene product produced which is encoded by the gene of interest. The quantity of mRNA produced by transcription of a selected nucleotide sequence can be determined for example by northern blot hybridisation, ribonuclease-RNA-protection, in situ hybridisation of cellular RNA or by PCR methods (Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994). Proteins which are encoded by a selected nucleotide sequence can also be determined by various methods such as, for example, ELISA, western blot, radioimmunoassay, immunoprecipitation, detection of the biological activity of the protein or by immune staining of the protein followed by FACS analysis (Sambrook, J. et al., Molecular Cloning: A Laboratory Manual Cold Spring Harbor Laboratory, Cold Spring Harbor, N.Y., 1989; Ausubel, F. M. et al., Current Protocols in molecular biology. New York: Greene Publishing Associates and Wiley-Interscience. 1994).

The terms "high expression level (or rate), high expression, increased expression or high productivity" refer to the long-lasting and sufficiently high expression or synthesis of a heterologous sequence introduced into a host cell, e.g. of a gene coding for a therapeutic protein. Increased or high expression or a high expression level or rate or a high productivity are present if a cell according to the invention is cultivated by one of the methods according to the invention described here and if this cell produces at least more than roughly 5 pg of the desired gene product per day (5 pg/day/cell). Increased or high expression or a high expression or rate or a high productivity are also present if the cell according to the invention produces at least more than roughly 10 pg of the desired gene produce per day (10 pg/day/cell). Increased or high expression or a high expression level or rate or high productivity are present in particular if the cell according to the invention produces at least more than roughly 15 pg of the desired gene product per day (15 pg/ day/cell). Increased or high expression or a high expression level or rate or high productivity are present in particular if the cell according to the invention produces at least more than roughly 20 pg of the desired gene product per day (20 pg/day/cell). Particularly increased or high expression or a particularly high expression level or rate or particularly high productivity are present if the cell according to the invention produces at least more than roughly 30 pg of the desired gene product per day (30 pg/day/cell).

High or increased expression, high productivity or a high expression level or rate according to the invention can be achieved in various ways. For example, through co-expression of the gene of interest with a gene for an amplifiable selectable marker it is possible to select and identify cells which express the heterologous gene to a high degree. The amplifiable selectable marker not only allows the selection of stably transfected host cells but also the gene amplification of the heterologous gene of interest. The additional copies of the nucleic acids may be integrated into the genome of the host cells, into additional artificial/mini-chromosomes or into episomally located polynucleotides. This procedure may be combined with a FACS-assisted selection of recombinant host cells which contain, as additional selectable marker, one or more fluorescent proteins (e.g. GFP) or a cell surface marker. Other methods of obtaining increased expression, and a combination of different methods may also be used, are based for example on the use of (artificial) transcription factors, treatment of the cells with natural or synthetic agents for up-regulating endogenous or heterologous gene expression, improving the stability (half-life) of mRNA or the protein, improving the initiation of mRNA translation, increasing the gene dose by the use of episomal plasmids (based on the use of viral sequences as replication origins, e.g. SV40, polyoma, adenovirus, EBV or BPV), the use of amplification-promoting sequences (Hemann, C. et al., *DNA Cell Biol* 1994, 13 (4), 437-445) or in vitro amplification systems based on DNA concatemers (Monaco, L. et al., *Gene* 1996, 180, 145-150).

According to the invention, coupled transcription of the gene of interest and of the gene which codes for the fluorescent protein is carried out. The resulting bicistronic mRNA expresses both the protein of interest and the fluorescent protein. On the basis of this coupling of the expression of the protein of interest and the fluorescent protein it is easily possible according to the invention to select and isolate high-producing recombinant host cells by means of the fluorescent protein expressed, e.g. by sorting using a fluorescence activated cell sorter (FACS).

The selection of recombinant host cells which exhibit high vitality and an increased expression rate of the desired gene product is a multistage process. The host cells which have been transfected with the expression vector according to the invention or optionally co-transfected with another vector, for example, are investigated at least for the expression of the gene which codes for a fluorescent protein and is coupled to the gene of interest, in order to identify and select the cells/cell population which exhibit the highest expression rates of fluorescent protein. Preferably, only the cells which belong to the 10% of cells with the highest expression rate of fluorescent protein are sorted out and further cultivated. In practice this means that the brightest 10% of the fluorescent cells are sorted out and further cultivated. Accordingly, the brightest 5%, preferably the brightest 3% or even the brightest 1% of the fluorescent cells of a cell mixture can also be sorted out and replicated. In a particularly preferred embodiment only the brightest 0.5% or the brightest 0.1% of the fluorescent cells are sorted out and replicated.

For this purpose, the cells which have previously been transformed with the expression vector according to the invention are cultivated in a selection medium which optionally also contains a selecting agent specific for the amplifiable selectable marker. Concentrations of selecting agent increasing step by step may be used to exert a gradually increasing selection pressure.

The selection step may be carried out on cell pools or using pre-sorted cell pools/cell clones. One or more, preferably two or more and especially three or more sorting steps may be carried out, while between the individual sorting steps the cells may be cultivated and replicated for a specific length of time, e.g. roughly two weeks in the case of pools.

If desired the host cells may be subjected to one or more gene amplification steps in order to increase the copy number of at least the gene of interest and the amplifiable selectable marker gene. Processes for step-by-step gene amplification using methotrexate are described for example in U.S. Pat. No. 5,179,017. According to the invention the high productivity which can be achieved is not tied to a high number of gene copies. Rather, it is the expression of increased stability and fermentation robustness in the high-performance clones. It is therefore possible to reduce the number of gene amplification steps required and to carry out only a single gene amplification, for example.

Accordingly, the invention thus relates to a method of selecting cells which comprises the following steps:
(i) transformation of suitable host cells at least with one of the vectors according to the invention, wherein the DNA of the expression vectors is preferably stably incorporated in the host cell genome or in artificial chromosomes/minichromosomes;
(ii) the transformed cells are cultivated under conditions which allow expression of the gene of interest and of the fluorescent protein;
(iii) the cells are cultivated in the presence of at least one selecting agent so that only those cells which are able to grow in the presence of the selecting agent are replicated;
(iv) the cells which exhibit the highest expression rate of fluorescent protein are sorted from a cell mixture, the cells being detected and sorted by means of a fluorescence-activated cell sorter (FACS);
(v) the sorted cells with the highest expression rates for the fluorescent protein are cultivated.

Optionally, steps ii)-v) can be repeated one or more times with the cells obtained according to step v). Moreover, the transformed cells may optionally also be subjected to one or more gene amplification steps by being cultivated in the presence of a selecting agent which leads to amplification of the amplifiable selectable marker gene. This step may be carried out both with cells which have not yet been sorted and also with cells which have already been pre-sorted one or more times.

The invention also relates to a process in which correspondingly sorted cells are replicated and used to prepare the coding gene product of interest. The selected high-producing cells are preferably cultivated in a serum-free culture medium and preferably in suspension culture under conditions which allow expression of the gene of interest. The protein of interest is preferably obtained from the cell culture medium as a secreted gene product. When the protein is expressed without a secretion signal, however, the gene product may also be isolated from cell lysates. In order to obtain a pure, homogeneous product which is substantially free from other recombinant proteins and host cell proteins, conventional purification steps are carried out. First of all, usually, cells and cell debris are removed from the culture medium or lysate. The desired gene product can then be freed from contaminating soluble proteins, polypeptides and nucleic acids, e.g. by fractionation on immunoaffinity and ion exchange columns, ethanol precipitation, reversed phase HPLC or chromatography on Sephadex, silica or cation exchange resins such as DEAE. Methods for purifying a heterologous protein expressed by recombinant cells are known to the skilled artisan and described in the literature (e.g. by Harris et al., Protein Purification: A Practical Approach, Pickwood and Hames, eds., IRL Press, 1995; Scopes, R., Protein Purification, Springer Verlag, 1988).

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

EXAMPLES

| Abbreviations | |
|---|---|
| AP: | alkaline phosphatase |
| bp: | base pair |
| CHO: | Chinese hamster ovary |
| DHFR: | dihydrofolate-reductase |
| ELISA: | enzyme-linked immunosorbant assay |
| FACS: | fluorescence-activated cell sorter |
| FAP: | fibroblast-activated protein |
| GFP: | green fluorescent protein |
| HBSS: | Hanks Balanced Salt Solution |
| HT: | hypoxanthine/thymidine |
| HRPO: | horseradish peroxidase |
| IRES: | internal ribosomal entry site |
| kb: | Kilobase |
| mAb: | monoclonal antibody |
| MTX: | methotrexate |
| PCR: | polymerase chain reaction |
| sICAM: | soluble intracellular adhesion molecule |

Methods

1. Cell Culture and Transfection

The cells CHO-DG44/dhfr−/− (Urlaub, G. et al., Cell 1983, 33, 405-412) were permanently cultivated as suspension cells in serum-free CHO-S-SFMII medium supplemented with hypoxanthine and thymidine (Invitrogen GmbH, Karlsruhe, Del.) in cell culture flasks at 37° C. in a damp atmosphere and 5% $CO_2$. The cell counts and viability were determined with a CASY1 Cell Counter (Schaerfe System, DE) or by tryptan blue staining and the cells were then seeded in a concentration of $1-3\times10^5$/mL and run every 2-3 days.

Lipofectamine Plus Reagent (Invitrogen GmbH) was used for the transfection of CHO-DG44. For each transfection mixture a total of 1 µg of plasmid-DNA, 4 µL of lipofectamine and 6 µL of Plus reagent were mixed together according to the manufacturer's instructions and added in a volume of 200 µL to $6\times10^5$ exponentially growing CHO-DG44 cells in 0.8 mL of HT-supplemented CHO-S-SFMII medium. After three hours of incubation at 37° C. in a cell incubator 2 mL of HT-supplemented CHO-S-SFMII medium was added. For the DHFR-based selection of stably transfected CHO-DG44 the cells were transferred 2 days after transfection into CHO-S-SFMII medium with no added hypoxanthine and thymidine, changing the medium every 3 to 4 days. In a DHFR- and neomycin phosphotransferase-based selection in the case of co-transfection in which one expression vector contained a DHFR and the other expression vector contained a neomycin-phosphotransferase selectable marker, G418 (Invitrogen) was also added to the medium in a concentration of 400 µg/mL.

A DHFR-based gene amplification of the integrated heterologous genes was obtained by the addition of the selecting agent MTX (Sigma, Deisenhofen, Del.) in a concentration of 5-2000 nM to the HT-free CHO-S-SFMII medium.

2. Expression Vectors

Figure 2:
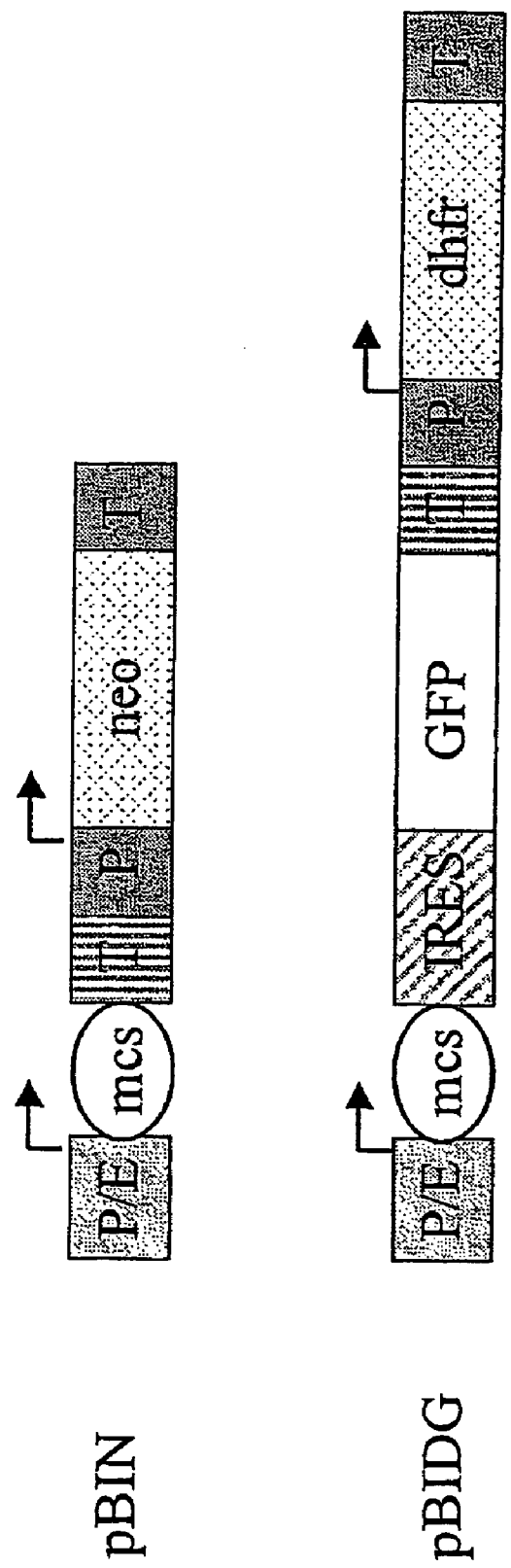
FIG. 2 shows a diagrammatic representation of the base vectors used to express the recombinant proteins in CHO-DG44 cells. "P/E" is a combination of CMV enhancer and hamster-ubiquitin/S27a promoter, "P" on its own indicates a promoter element and "T" is a termination signal for transcription, which is needed for the polyadenylation of the transcribed mRNA. The position and direction of transcription initiation within each transcription unit is indicated by an arrow. For cloning the heterologous genes a sequence region with multiple cutting sites for restriction endonucleases (multiple cloning sites—mcs) is inserted after the promoter element. The amplifiable selectable marker dihydrofolate reductase is abbreviated to "dhfr" and the selectable marker neomycin phosphotransferase is abbreviated to "neo". The "IRES" element coming from the encephalomyocarditic virus acts as an internal ribosomal entry site within the bicistronic transcription unit and enables translation of the following green fluorescent protein "GFP".

To analyse the expression, eukaryotic expression vectors were used which are based on the pAD-CMV vector (Werner, R. G. et al., Arzneim.-Forsch./Drug.Res. 1998, 48, 870-880) and mediate the constitutive expression of a heterologous gene by the combination of CMV enhancer/hamster ubiquitin/S27a promoter (WO 97/15664). While the base vector pBID contains the DHFR minigene which acts as an amplifiable selectable marker (cf e.g. EP 0 393 438), in the vector pBIN the DHFR minigene has been replaced by a neomycin resistance gene (FIG. 2). For this purpose the selectable marker neomycin-phosphotransferase, including SV40 early promoter and TK-polyadenylation signal, was isolated from the commercial plasmid pBK-CMV (Stratagene, La Jolla, Calif., USA) as a 1640 bp Bsu36I fragment. After a reaction to fill in the ends of the fragment with Klenow-DNA-polymerase the fragment was ligated with the 3750 bp Bsu36I/StuI fragment of the vector pBID, which was also treated with Klenow-DNA-polymerase.

In the bicistronic base vector pBIDG (FIG. 2) the IRES-GFP gene region was isolated from the vector pIRES2-EGFP (Clontech, Palo Alto, Calif., USA) and brought under the control of the CMV enhancer/promoter in the vector pBID so that the multiple cloning site between the promoter region and IRES-element was retained. The following procedure was used. In a PCR mutagenesis in which the plasmid pIRES2-EGFP acted as the template, on the one hand the HindIII cutting site AAGCTT within the IRES sequence was converted into the sequence ATGCTT by the use of mutagenic primers and thus eliminated. On the other hand an XbaI cutting site was inserted by means of a primer with complementarity to the 5'end of the IRES sequence or a SpeI cutting site was introduced by means of a primer with complementarity to the 3'end of the GFP sequence. The resulting PCR fragment, which contained the complete IRES and GFP sequence, was digested with XbaI and SpeI and cloned into the singular XbaI cutting site at the 3'end of the multiple cloning site of the vector pBID.

The human sICAM gene was isolated as a HindIII/SalI fragment from pAD-sICAM (Werner, R. G. et al., *Arzneim.-Forsch./Drug.Res.* 1998, 48, 870-880) and cloned into the corresponding cutting sites of the vector pBIDG, resulting in the vector pBIDG-sICAM (FIG. 3).

In order to express the monoclonal humanised F19 antibody the heavy chain was isolated as a 1.5 kb NaeI/HindIII fragment from the plasmid pG1D105F19HC (NAGENESEQ: AAZ32786) and cloned into the vector pBIDG digested with EcoRI (filled in with Klenow-DNA-polymerase) and HindIII, resulting in the vector pBIDG-F19HC (FIG. 3). The light chain on the other hand was isolated as a 1.3 kb HindIII/EcoRI fragment from the plasmid pKN100F19LC (NAGENESEQ: AAZ32784) and cloned into the corresponding cutting sites of the vector pBIN, producing the vector pBIN-F19LC (FIG. 3).

3. FACS

The flow-cytometric analyses and sorting were carried out with a Coulter Epics Altra device. The FACS is fitted with a helium-argon laser with an excitation wavelength of 488 nm. The fluorescence intensity is absorbed at a wavelength suited to the fluorescence protein and process by means of the attached software Coulter Expo32. The sorting was carried out at a rate of 8000-10000 events/second. The suspended cells were centrifuged (5 min at 180×g) and adjusted to a cell concentration of 1-1.5×10$^7$/mL in HBSS. Then the cells were sorted according to their fluorescence protein signal. The cells were taken up in test tubes already containing culture medium, then centrifuged and seeded into suitable culture vessels depending on the number of cells sorted.

4. ELISA

The sICAM titres in supernatants of stably transfected CHO-DG44 cells were quantified by ELISA according to standard procedures (Ausubel, F. M. et al., Current Protocols in molecular biology. New York: Greene Publishing Associates and Wiley-Interscience. 1994), using on the one hand a goat anti human IgG Fc fragment (Dianova, Hamburg, Del.) and on the other hand an AP-conjugated goat anti human kappa light chain antibody (Sigma). Purified F19 antibody was used as the standard.

Productivities (pg/cell/day) were calculated by the formula pg/((Ct-Co) t/ln (Ct-Co)), where Co and Ct are the cell count on seeding and harvest, respectively, and t is the cultivation time.

Example 1

Comparison of the CMV and Hamster-ubiquitin/S27a-Promoter Activity

In order to compare the activity of the hamster-ubiquitin/S27a-promoters with that of the CMV promoter frequently used in eukaryotic expression vectors, CHO-DG44 cells were transfected with various recombinant vectors. The heterologous gene product, on the one hand a lysosomal enzyme, on the other hand an IgG1-antibody, was expressed either under the control of the CMV-promoter or under the control of the hamster-ubiquitin/S27a-promoter. The two promoters were functionally linked to the CMV-enhancer. BGH polyA was used as the termination signal for the heterologous gene. The expression vectors which contained the CMV-promoter were based either on a modified pcDNA3 ("CMV$^1$", Invitrogen) or pBluescript vector ("CMV$^2$", Stratagene) and additionally coded for the amplifiable selectable marker dihydrofolate-reductase. The expression vector with the hamster promoter on the other had was based on the pAD-CVM vector (Werner, R. G. et al., *Arzneim.-Forsch./Drug.Res.* 1998, 48, 870-880). In order to express the heavy and light chain of the antibody, cotransfection was carried out with a second vector which contained a neomycin resistance gene as selectable marker. The CMV enhancer may, however, also be replaced by the SV40 enhancer.

By limited dilution in 96 well plates, after transfection, cell clones were selected and isolated in HT-free medium (with the addition of 400 µg/mL G418 in the case of co-transfection). Cell clones with the highest productivity with respect to the recombinant protein were subjected to stepwise DHFR-based gene amplification by increasing the methotrexate concentration step by step from 5 nM via 50 nM, 500 nM to 2 µM, in conjunction with a diluting cloning in each case. At each amplification stage about 20 to 30 clones with the highest productivity were selected.

Figure 1:
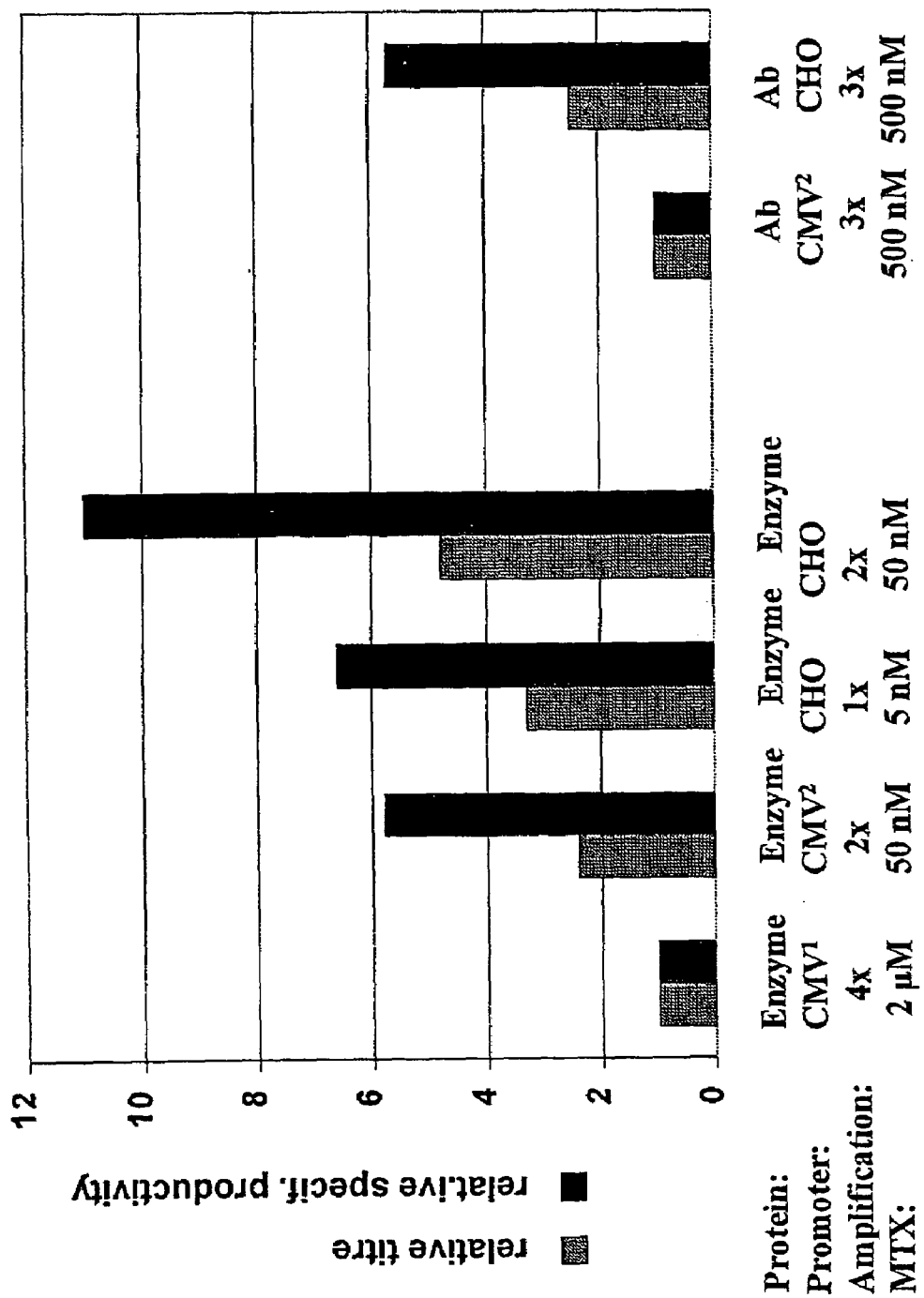
FIG. 1 shows a comparison of the expression levels obtained with recombinant cell clones in which the heterologous gene product is expressed either under the control of the CMV promoter or under the control of a hamster-ubiquitin/S27a promoter. The two promoters are functionally linked to the CMV enhancer and the termination sequence, BGH poly A, is identical in every case. In the case of $CMV^1$ the expression vector is pcDNA3-based (Invitrogen, Kalsruhe, Del.), in $CMV^2$ it is a pBluescript-based expression vector (Stratagene, La Jolla, Calif., US) and in the case of CHO it is a pAD-CMV-based expression vector (Werner, R. G. et al., Arzneim.-Forsch./Drug.Res. 1998, 48, 870-880). In the expression of the lysosomal enzyme, all the expression vectors contain the amplifiable selectable marker dihydrofolate reductase (DHFR) and the expression of the heterologous gene has been increased by subsequent amplification steps with methotrexate (MTX). In order to express the two chains of the antibody (Ab) co-transfection has been carried out with a second vector which contains a neomycin-resistance gene as the selectable marker. The titres or specific productivities obtained are given in relation to the CMV promoter-based expression, which is set at 1 ($CMV^1$ for enzyme, $CMV^2$ for Ab).

Generally, the hamster promoter was found to have the highest performance. Both in the expression of the lysosomal enzyme and also in the expression of the antibody, productivities or titres were obtained which were 2 to 5 times higher than those obtained with cells in which the heterologous gene was expressed under the control of the CMV promoter. FIG. 1 shows by way of example the relative titres and relative specific productivities of the best cell clones at that particular amplification stage, the expression for the particular heterologous gene based on the CMV promoter being set at 1 (CMV$^1$ for the lysosomal enzyme, CMV$^2$ for the antibody).

Example 2

Isolation of High-expressing sICAM Cells by GFP-based FACS Sorting

The soluble form of the intercellular adhesion molecule ICAM1, sICAM, is a possible treatment for colds as it competes with the ICAM receptor for the binding of rhinoviruses and in this way can reduce or even prevent their interaction with the ICAM receptor, the prerequisite for entry into the cells and subsequent infection (Bella, J. et al., *J. Struct. Biol.* 1999,128, 69-74; Marlin, S. D. et al., *Nature* 1990, 344, 70-77).

sICAM was chosen as an example for the expression of a single-chained protein (480 amino acids) in CHO cells. For this CHO-DG44 were transfected with pBIDG-sICAM (FIG. 3). The additional expression of GFP in pBIDG-sICAM transfected cells made it possible to use a FACS-based selection strategy. The therapeutic protein sICAM and GFP were jointly expressed by a bicistronic transcription unit and the DHFR by a separate transcription unit. Two to three weeks after the first selection in HT-free CHO-S-SFMII medium, 5% of the cells with the highest GFP fluorescence were sorted out. After about two weeks of cultivation the 5% cells with the highest GFP fluorescence were again isolated. This sequential sorting was carried out six times in all. A good correlation could be demonstrated between sICAM productivity and GFP fluorescence (FIG. 4). By FACS-assisted selection alone, without any MTX amplification step, cell pools with high specific productivities of up to 16 pg/cell/day were thus isolated in a very short time (FIG. 5). By combining the GFP-based selection with a single subsequent MTX amplification step it was even possible to increase productivity to above 30 pg/cell/day (FIG. 6). These productivities were achieved both with an amplification of a pool after the fourth sort with 500 nM MTX and also after amplification of a pool after the sixth sort with 2 μM MTX. In contrast to a stepwise amplification which usually starts with very low MTX concentrations in the range from 5-20 nM MTX, a higher MTX concentration had to be used from the outset to achieve an amplification effect. Thus, there was no significant increase in productivity as a result of the addition of 5 or 50 nM of MTX to cells from the fourth sorting or as a result of the addition of 500 nM of MTX t cells from the sixth sorting (FIG. 6). Obviously, the level of DHFT in the starting pools was already so high that total DHFR inhibition could only be achieved with a high dose of MTX. Moreover, the pre-sorted cell pools survived the selection phase much better in spite of the high initial dose of MTX, i.e. a cell population of high vitality was obtained in a shorter time than with the conventional step-by-step gene amplification strategy (FIG. 7).

Example 3

Isolation of Cells With High Expression of the mAb F19 by GFP-based FACS Sorting In a co-transfection CHO-DG44 cells were transfected with the plasmid combination pBIDG-F19HC and pBIN-F19LC (FIG. 3). The expressed humanised antibody F19 is directed against the surface molecule FAP which is synthesized by reactive stroma fibroblasts (cf also EP 0 953 639). In the vector configurations used the two protein chains of the antibody are expressed by their own vector, which additionally also codes for a DHFR or neomycin-phosphotransferase selectable marker in a separate transcription unit. In addition, another selectable marker, GFP, is contained in the vector pBIDG-F19HC. By the transcriptional linking of the expression of the GFP and the heavy chain by means of an IRES element, in the co-transfection of CHO-DG44 with the vectors pBIDG-F19HC/pBIN-F19LC, cells with a high expression of the antibody F19 could rapidly be isolated solely by selecting the cells with a high GFP content using sequential FACS sorting. For this, after a first two- to three-week selection of the transfected cell pools in HT-free CHO-S-SFMII medium with the addition of 400 μg/mL of G418, the 5% of cells with the highest GFP fluorescence were sorted out by FACS. This sorting was carried out up to six times in all, leaving a cultivation period of about 2 weeks between each sorting. Astonishingly there was found to be a good correlation between F19 productivity and GFP fluorescence (FIG. 8), although both protein chains were expressed from their own vector and in the GFP-based FACS sorting it was only possible to select for the expression of the heavy chain, as a result of its transcriptional coupling with GFP. The productivities could be increased to 10 pg/cell/day (FIG. 9) and further increased to an average of 37 pg/cell/day by a single subsequent MTX amplification step, starting from the cell pool of the fifth sorting, by adding 1000 nM MTX to the selection medium. Comparable data could also be obtained by functionally linking the hamster promoter with the SV40 enhancer instead of the CMV enhancer. At the same time, the development time for selecting high-producing cells in comparison with a conventional stepwise gene amplification strategy, which generally comprises four amplification stages, with increasing amounts of MTX, could be reduced by half to about 120 days, with a concomitant significant reduction in the development capacities and costs.

Various patent applications and publications are cited herein, the disclosures of which are incorporated by reference in their entireties.

What is claimed is:

1. A process for selecting a host cell which expresses a protein/product of interest comprising:
   (i) cultivating a population of eukaryotic host cells which have been transfected with an expression vector comprising:
      (a) a gene which codes for a protein/product of interest, functionally linked to a hamster-ubiquitin/S27a-promoter; and
      (b) a gene which codes for a fluorescent protein;
      under conditions which allow expression of the protein/product of interest and of the fluorescent protein;
   (ii) isolating cell pools which achieve average specific protein/product productivities of more than 10 pg of recombinant protein/product expression per cell per day without gene amplification and
   (iii) selecting host cell clones which show the highest expression levels of fluorescent protein.

2. The process according to claim 1, wherein selecting the host cell clones comprises using a Fluorescence-Activated Cell Sorter (FACS).

3. The process according to claim 1, further comprising subjecting the selected host cells clones to one or more gene amplification steps in the presence of an amplifying agent.

4. The process according to claim 3, wherein the expression vector further comprises the amplifiable selectable marker is dihydrofolate reductase (DHFR) and the amplifying agent is methotrexate.

5. The process according to claim 1, wherein the population of host cells is cultured in serum-free culture medium.

6. The process according to claim 1, wherein the population of host cells is cultivated in suspension culture.

7. The process according to claim 1, wherein the process further comprises the preparation of a heterologous gene product by
   (iv) cultivating a host cell under conditions which allow expression of the protein/product of interest and
   (v) isolating the gene product form the culture or culture medium.

8. The process according to claim 6, wherein the heterologous gene product is a heteromeric protein/product, whereby the host cell has been co-transfected with expression vectors which code for the different subunits of the heteromeric proteins/products.

9. The process according to claim 7, wherein the heteromeric protein/product is an antibody.

10. The process according to claim 1, wherein the host cell is a Chinese hamster ovary (CHO) cell.

11. The process according to claim 6, wherein the host cell is a Chinese hamster ovary (CHO) cell.

* * * * *